US007285410B2

(12) United States Patent
Bramucci et al.

(10) Patent No.: US 7,285,410 B2
(45) Date of Patent: Oct. 23, 2007

(54) PREPARATION OF (E)- AND (Z)-2-METHYL-2-BUTENOIC ACIDS

(75) Inventors: Michael G. Bramucci, Folsom, PA (US); Robert DiCosimo, Chadds Ford, PA (US); Sarita Chauhan, Landenberg, PA (US); Robert D. Fallon, Elkton, MD (US); John E. Gavagan, Wilmington, DE (US); Mark S. Payne, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/585,036

(22) Filed: Oct. 23, 2006

(65) Prior Publication Data

US 2007/0037264 A1    Feb. 15, 2007

Related U.S. Application Data

(62) Division of application No. 11/338,471, filed on Jan. 24, 2006, now Pat. No. 7,220,562, which is a division of application No. 10/431,965, filed on May 8, 2003, now Pat. No. 7,198,926.

(51) Int. Cl.
  C12N 1/20      (2006.01)
  C12N 9/78      (2006.01)
  C12N 9/88      (2006.01)
  C12N 15/00     (2006.01)
  C12Q 1/34      (2006.01)
  C07K 14/00     (2006.01)
  C07H 21/04     (2006.01)

(52) U.S. Cl. ............... 435/252.3; 435/227; 435/18; 435/320.1; 435/232; 536/23.2; 530/350

(58) Field of Classification Search ............ 435/252.3, 435/227, 18, 320.1, 232; 536/23.2; 530/350
See application file for complete search history.

(56) References Cited

U.S. PATENT DOCUMENTS 5,041,646 A    8/1991   Gebauer
5,998,180 A    12/1999  Armitage et al.

FOREIGN PATENT DOCUMENTS

CA    2103616        2/1994
WO    WO 03/000640 A2    1/2003
WO    WO 03/14356 A1    2/2003

OTHER PUBLICATIONS

Franz Effenberger et al., Tetrahedron: Asymmetry, 12:2581-2587 (2001), (G)-Selective hydrolysis of (E,Z)-alpha, Beta-unsaturated nitriles by the recombinant nitrilase AlNIT1 from *Arabidopsis thaliana*.
Robert E. Buckles et al., J. Org. Chem., 15:680-684 (1950), The Preparation of Tiglic and Angelic Acids and Esters.
H. Alper et al., Tetrahedron Lett. 30(20):2815-2816, 1969, Stereospecific Nickel and Phase Transfer Catalyzed Carbonylation of Vinyl Bromides and Chlorides.
S. W. Pelletier et al., J. Am. Chem. Soc., 74:6292-6293, 1952, The Ultraviolet-induced Isomerization of Tiglic Acid to Agnelic Acid.
Michihiko Kobayashi et al., Tetrahedron 46:5587-5590, 1990, Monohydrolysis of an Aliphatic Dinitrile Compound by Nitrilase from *Rhodococcus rhodochrous* K22.
Michihiko Kobayashi et al., J. Bacteriology, 172:4607-4615, 1990, Purification and Cahracterization of a Novel Nitrilase of *Rhodococcus rhodochrous* K22 That Acts on Aliphatic Nitriles.
S. Levy-Schil et al., Gene, 161;15-20, 1995, Aliphatic nitrilase from a soil-isolated *Comamones testosteroni* sp.:gene cloning and overexpression, purification and primary structure.
John E. Gavagan et al., J. Org. Chem., 63:4792-4801, 1998, Chemoenzymic Production of Lactame from Aliphatic alpha, w-Dinitriles.
Don Cowen et al., Extremophiles, 2:207-216, 1998, Biochemistry and biotechnology of mesophilic and thermophilic nitrile metabolizing enzymes.
Sheng-Min Zhao et al., Chinese J. Chem., 20:1291-1299, 2000, Synthesis of Optically Active beta-Alkyl-alpha-methylane-y-butyro-lactones from Enantioselective Biotransformation of Nitriles, an Unusual Inversion of Enantioselectivity.
Qadrayah A. Almatawah et al., Extremephiles, 3:283-291, 1999, Characterization of an inducible nitrilase from a thermophilic bacillus.
Masahiro Miura et al., J. Chem. Soc., Perkin Transactions 1 (1):73-76, 1989, Carbonylation of Vinyl Halides with Caronbylcobalt.
Michihiko Kobayashi et al., Eur. J. Biochem., vol. 217:327, 1993, Amidase coupled with low-molecular-mass nitrile hydratase from *Rhodococcus rhodochrous* J1.
Ludmila Martinkova et al., Biocatalysis and Biotransformation 20:73-93 (2002). Nitrile-and Amideconverting Microbial Enzymes: Stereo-, Regio- and Chemoselectivity.
Branden et al., Introduction to Protein Structure, Garland Publishing Inc., new York, p. 247, 1991. Prediction, Engineering, And Design of Protein Structures.
Jennifer L. Seffernick et al., Journal of Bacteriology, vol. 163(6):2405-2410, 2001, Melamine Deaminase and Atrazine Chlorohydrolase: 98 Percent Identical but Functionally Different.
Andrzaj Witkowski et al., Biochemistry, vol. 38:11643-11650, 1999, Conversion of a beta-Ketoacyl Synthase to a Malonyl Decarboxylase by Replacement of the Active-Site Cystine with Glutamine.

*Primary Examiner*—Delia M. Ramirez

(57) ABSTRACT

A method has been developed to prepare (E)- and (Z)-2-methyl-2-butenoic acids (2M2BA) from a mixture of (E,Z)-2-methyl-2-butenenitriles (2M2BN) by the regioselective hydrolysis of (E)-2M2BN to (E)-2-methyl-2-butenoic acid (2M2BA) using enzyme catalysts having either a nitrilase activity or a combination of nitrile hydratase and amidase activities. The method provides high yields without significant conversion of (Z)-2M2BN to (Z)-2M2BA. The regioselective hydrolysis of (E)-2M2BN to (E)-2M2BA makes possible the facile separation of (E)-2M2BA from (Z)-2M2BN or (Z)-2-methyl-2-butenamide (2M2BAm), and the subsequent conversion of (Z)-2M2BN or (Z)-2M2BAm to (Z)-2M2BA.

2 Claims, No Drawings

PREPARATION OF (E)- AND (Z)-2-METHYL-2-BUTENOIC ACIDS

CROSS-REFERENCE TO RELATED APPLICATION

This is a divisional of U.S. patent application Ser. No. 11/338,471 filed Jan. 24, 2006, now U.S. Pat. No. 7,220,562, which is a divisional of U.S. patent application Ser. No. 10/431,965, filed May 8, 2003, now U.S. Pat. No. 7,198,926.

FIELD OF THE INVENTION

The present invention relates to a biocatalytic, regioselective method for preparing (E)- and (Z)-2-methyl-2-butenoic acids (2M2BA) in high yields and two new microbial catalyst compositions useful in the method.

BACKGROUND OF THE INVENTION (E)-2-methyl-2-buteneoic acid ((E)-2M2BA) (commonly known as tiglic acid) and (Z)-2-methyl-2-buteneoic acid ((Z)-2M2BA) (commonly known as angelic acid) are useful starting materials for preparing flavors and fragrances, and for preparing pharmaceutical intermediates.

(Z)-2M2BA has been prepared by the oxidation of the corresponding (Z)-alcohol with manganese dioxide, followed by the oxidation of the resulting aldehyde with sodium chlorite in the presence of hydrogen peroxide and sodium hydrogen phosphate (M. Zaidlewicz, Z. Walasek, PL 169502 B1 (1996)). R. E. Buckles and G. V. Mock reported the preparation of (E)-2M2BA in 53% yield by the action of 100% sulfuric acid on 2-hydroxy-2-methylbutyronitrile, followed by hydrolysis of the resulting (E)-2-methyl-2-butenamide (*J. Org. Chem.*, 15:680-684 (1950)). The (E)-2M2BA produced by the Buckles-Mock process was further converted to (Z)-2M2BA in 33% yield by bromination of (E)-2M2BA to 2,3-dibromo-2-methylbutyric acid, debromination to (Z)-2-bromo-2-methylbutenoic acid using methanolic potassium hydroxide, followed by reduction of the bromo-acid using sodium amalgam.

(E)-2M2BA has been prepared in 89% yield by the carbonylation of 2-chloro-2-butene using catalytic quantities of cetyltrimethylammonium bromide and nickel cyanide (H. Alper et al., *Tetrahedron Lett.*, 30:2615-2616 (1989)). Similarly, treatment of (E)- or (Z)-2-bromo-2-butene with carbon monoxide and octacarbonyldicolbalt in the presence of methyl iodide and calcium hydroxide in dioxane-water gave only (E)-2M2BA in 87-88% yield (M. Masahiro et al., *J. Chem. Soc.*, Perkin Transactions 1 (1):73-76 (1989)). (E)-2M2BA has also been produced in 3% yield by UV irradiation of (Z)-2M2BA for 43 days, followed by separation of the (E)- and (Z)-isomers by a combination of fractional crystallizations and extractions (S. W. Pelletier and W. L. McLeish, *J. Am. Chem. Soc.*, 74:6292-6293 (1952)).

Nitriles are readily converted to the corresponding carboxylic acids by a variety of chemical processes, but these processes typically require strongly acidic or basic reaction conditions, high reaction temperatures, and produce unwanted byproducts and/or large amounts of inorganic salts as unwanted waste. These chemical processes for nitrile hydrolysis are not known to result in the regioselective hydrolysis of mixtures of geometric isomers of nitriles. U.S. Pat. No. 5,041,646 describes a process where (E,Z)-2M2BN is reacted with sulfuric acid at elevated temperatures, followed by distillation of the product mixture to produce a mixture of 80.5% (Z)-2M2BA and 19.5% (E)-2M2BA; pure (Z)-2M2BA was prepared by fractional crystallization of the (E,Z)-2M2BA mixture. 2-Methyl-3-butenenitrile (2M3BN), a commercially-available by-product produced during the manufacture of adiponitrile by hydrocyanation of butadiene, is readily isomerized to a mixture of (E)-2M2BN and (Z)-2M2BN, but separating this mixture by distillation is difficult and expensive due to the similar boiling points and chemical properties of the geometric isomers.

The enzyme-catalyzed hydrolysis of nitrile-containing substrates to the corresponding carboxylic acids is often preferred to chemical methods because the reactions are often run at ambient temperature, do not require the use of strongly acidic or basic reaction conditions, and produce the desired product with high selectivity at high conversion.

A nitrilase enzyme directly converts a nitrile to the corresponding carboxylic acid ammonium salt in aqueous solution without the intermediate formation of an amide. Nitrilases have been identified in a variety of microorganisms. For example, Kobayashi et al. (*Tetrahedron* 46:5587-5590 (1990); *J. Bacteriology*, 172:4807-4815 (1990)) have described an aliphatic nitrilase isolated from *Rhodococcus rhodochrous* K22 that catalyzed the hydrolysis of aliphatic nitriles to their corresponding carboxylic acid ammonium salts. A nitrilase from *Rhodococcus rhodochrous* NCIMB 40757 or NCIMB 40833 has been used to convert acrylonitrile to ammonium acrylate (U.S. Pat. No. 5,998,180). A nitrilase from *Comamonas testosteroni* has been isolated that can convert a range of aliphatic α,ω-dinitriles to either the corresponding ω-cyanocarboxylic acid ammonium salt or dicarboxylic acid diammonium salt (CA 2,103,616; S. Lévy-Schil et al., *Gene*, 161:15-20 (1995)). The regioselective hydrolysis of aliphatic α,ω-dinitriles to the corresponding ω-cyanocarboxylic acid ammonium salts by the nitrilase activity of *Acidovorax facilis* 72W has also been reported (Gavagan et al., *J. Org. Chem.*, 63:4792-4801 (1998)). The nitrilase gene from *Arthrobacter* sp. NSSC104 has been cloned (WO 0314355), and a variety of bacterial nitrilases exhibiting stereoselectivity have been identified (WO 0300840).

A combination of two enzymes, nitrile hydratase and amidase, can also be used to convert aliphatic nitrites to the corresponding carboxylic acid ammonium salts in aqueous solution. Here the aliphatic nitrile is initially converted to an amide by the nitrile hydratase and then the amide is subsequently converted by the amidase to the corresponding carboxylic acid ammonium salt. Bacterial genera (including *Rhodococcus*, *Pseudomonas*, *Alcaligenes*, *Arthrobacter*, *Bacillus*, *Bacteridium*, *Brevibacterium*, *Corynebacterium*, and *Micrococcus*) are known to possess a broad spectrum of various nitrile hydratase and amidase activities. Cowan et al. (*Extremophiles*, 2:207-216 (1998)) and Martinkova and Kren (*Biocatalysis and Biotransformation*, 20:73-93 (2002)) have reviewed the nitrilase and nitrile hydratase/amidase enzyme systems of nitrile-degrading microorganisms.

Effenberger and Osswald (*Tetrahedron*, 12:2581-2587 (2001)) have reported the (E)-selective hydrolysis of (E,Z)-α,β-unsaturated nitrites by the recombinant nitrilase AtNIT1 from *Arabidopsis thaliana*, where the (E)-isomer of the (E,Z)-3-substituted-acrylonitrile mixtures was exclusively hydrolyzed in the presence of the corresponding (Z)-isomer; no 2,3-disubstituted acrylonitriles were examined as substrate for this nitrilase. When (E,Z)-3-heptenenitrile was used as substrate with this same nitrilase, enrichment of one isomer was not observed for either nitrile or acid. Almatawah et al. (*Extremophiles*, 3:283-291 (1999)) have reported that the nitrilase of *Bacillus pallidus* Dac521 showed no activity for hydrolysis of cis-2-pentenenitrile, but was capable of hydrolyzing acrylonitrile, methacrylonitrile, or crotononitrile; no 2,3-disubstituted acrylonitriles were examined as substrate for this nitrilase. Zhao and Wang (*Chinese J. Chem.*, 20:1291-1299 (2002)) demonstrated that the combined nitrile hydratase and amidase activities of *Rhodococcus* sp. AJ270 could be used for the enantioselective biotransformation of racemic β-substituted-α-methylenepropionitriles. Where the amidase was shown by Zhao and Wang supra to discriminate between the two amide hydration products produced by the nitrile hydratase, no 2,3-disubstituted acrylonitriles were examined as substrate for this combination of nitrile hydratase/amidase enzymes.

The problem to be solved, therefore, is the lack of a process for the facile preparation of (E)- and (Z)-2M2BA from a mixture of (E,Z)-2M2BN using an enzyme catalyst having either nitrilase activity or a combination of nitrile hydratase and amidase activities, where the enzyme catalyst is regioselective for the hydrolysis or hydration of one of the two geometric isomers of (E,Z)-2M2BN.

SUMMARY OF THE INVENTION

A process is disclosed for preparing (E)- and (Z)-2-methyl-2-butenoic acids (2M2BA) in high yield and purity from a mixture of (E,Z)-2-methyl-2-butenenitriles (2M2BN) by the regioselective hydrolysis of (E)-2M2BN to (E)-2-methyl-2-butenoic acid (2M2BA), without significant conversion of (Z)-2M2BN to (Z)-2M2BA. The invention has the steps of (a) contacting (E,Z)-2M2BN in an aqueous reaction mixture with an enzyme catalyst expressing a regioselective nitrilase activity; (b) separating the (E)-2M2BA produced in step (a) from unreacted (Z)-2M2BN, and (c) converting (Z)-2M2BN to (Z)-2M2BA. More particularly, (E)-2M2BN is converted to the corresponding carboxylic acid (as the ammonium salt) with high regioselectivity at 100% conversion, using a regioselective nitrilase as catalyst. The regioselective hydrolysis of (E)-2M2BN to (E)-2M2BA (as the ammonium salt) makes possible the facile separation of (E)-2M2BA from (Z)-2M2BN, and for the subsequent conversion of (Z)-2M2BN to (Z)-2M2BA in high yield and purity.

Microorganisms characterized by a nitrilase activity and useful in the process are *Acidovorax facilis* 72-PF-15 (ATCC 55747) and *Acidovorax facilis* 72-PF-1 7 (ATCC 55745). Additionally, transformed microbial cells containing *A. facilis* 72W nitrilase activity are included in this invention. *Escherichia coli* SS1001 (ATCC PTA-1177) and *Escherichia coli* SW91 (ATCC PTA-1175) are examples of such a transformed microbial cell catalyst.

A further embodiment of the invention is the use of the *A. facilis* 72W (ATCC 55746) strain that expresses (1) regioselective and chemoselective nitrilase activity and (2) a non-regioselective nitrile hydratase and amidase activity, as an enzyme catalyst for regioselective hydrolysis of (E)-2M2BN to (E)-2M2BA. Prior to use as catalyst, whole *A. facilis* 72W (ATCC 55746) microbial cells are heated to a temperature of about 35° C. to 70° C. for between 10 and 120 minutes, whereby the non-regioselective nitrile hydratase and amidase activity is destroyed and the regioselective nitrilase activity is preserved. Where the transformed whole microbial cell expresses regioselective and chemoselective nitrilase activity and lacks the non-regioselective nitrile hydratase and amidase activities, no heat-treatment step is needed. *Escherichia coli* SS1001 (ATCC PTA-1177) and *Escherichia coli* SW91 (ATCC PTA-1175) are examples of a transformed microbial cell catalyst that lack non-regioselective nitrile hydratase and amidase activities.

A further embodiment of the invention uses a catalyst having a combination of a regioselective nitrile hydratase and amidase activities. The invention has the steps of (a) contacting (E,Z)-2M2BN in an aqueous reaction mixture with an enzyme catalyst expressing a combination of regioselective nitrile hydratase and amidase activities; (b) separating the (E)-2M2BA produced in step (a) from unreacted (Z)-2M2BN and/or (Z)-2M2BAm, and (c) conversion of (Z)-2M2BN and/or (Z)-2M2BAm to (Z)-2M2BA. More particularly, (E)-2M2BN is converted to the corresponding carboxylic acid (as the ammonium salt) with high regioselectivity at 100% conversion, by a combination of regioselective nitrile hydratase and amidase activities derived from the group of microbial catalysts consisting of *Comamonas testosteroni* 5-MGAM4D, *Comamonas testosteroni* S2B-1 (ATCC PTA-5135), and *Comamonas testosteroni* S5C (ATCC PTA-5134). The regioselective hydrolysis of (E)-2M2BN to (E)-2M2BA makes possible the facile separation of (E)-2M2BA from unreacted (Z)-2M2BN and/or (Z)-2M2BAm), and for the subsequent conversion of (Z)-2M2BN and/or (Z)-2M2BAm to (Z)-2M2BA.

Further embodiments of the invention use an enzyme catalyst in the form of intact microbial cells, permeabilized microbial cells, one or more cell components of a microbial cell extract, and partially-purified enzyme(s), or purified enzyme(s). These different forms of enzyme catalyst can be immobilized on or in a soluble or insoluble support using techniques well-known to those skilled in the art.

SEQUENCE DESCRIPTIONS

The invention can be more fully understood from the following detailed description, biological deposits, and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence encoding a nitrilase isolated from *Acidovorax facilis* 72W (ATCC 55746).

SEQ ID NO:2 is the deduced amino acid sequence of a nitrilase isolated from *Acidovorax facilis* 72W.

SEQ ID NO:3 is the nucleotide sequence encoding a nitrilase expressed in *Escherichia coli* SS1001 (ATCC PTA-1177).

SEQ ID NO:4 is the deduced amino acid sequence of a nitrilase expressed in *Escherichia coli* SS1001.

SEQ ID NO:5 is the nucleotide sequence encoding the α-subunit of a nitrilase hydratase isolated from *Comamonas testosteroni* 5-MGAM-4D (ATCC 55744).

SEQ ID NO:6 is the deduced amino acid sequence of the nitrile hydratase α-subunit isolated from *Comamonas testosteroni* 5-MGAM-4D.

SEQ ID NO:7 is the nucleotide sequence encoding the β-subunit of a nitrilase hydratase isolated from *Comamonas testosteroni* 5-MGAM-4D.

SEQ ID NO:8 is the deduced amino acid sequence of the nitrile hydratase β-subunit isolated from *Comamonas testosteroni* 5-MGAM-4D.

SEQ ID NO:9 is the nucleotide sequence encoding an amidase isolated from *Comamonas testosteroni* 5-MGAM4D.

SEQ ID NO:10 is the deduced amino acid sequence of the amidase isolated from *Comamonas testosteroni* 5-MGAM-4D.

BRIEF DESCRIPTION OF THE BIOLOGICAL DEPOSITS

Applicants have made the following biological deposits under the terms of the Budapest Treaty on the International Recognition of the Deposit of Microorganisms for the Purposes of Patent Procedure:

| Depositor Identification Reference | Int'l. Depository Designation | Date of Deposit |
|---|---|---|
| *Acidovorax facilis* 72-PF-17 | ATCC 55745 | 8 Mar. 1996 |
| *Acidovorax facilis* 72W | ATCC 55746 | 8 Mar. 1996 |
| *Acidovorax facilis* 72-PF-15 | ATCC 55747 | 8 Mar. 1996 |
| *Escherichia coli* SS1001 | ATCC PTA-1177 | 11 Jan. 2000 |
| *Escherichia coli* SW91 | ATCC PTA-1175 | 11 Jan. 2000 |
| *Comamonas testosteroni* 5-MGAM-4D | ATCC 55744 | 8 Mar. 1996 |
| *Comamonas testosteroni* S2B-1 | ATCC PTA-5135 | 11 Apr. 2003 |
| *Comamonas testosteroni* S5C | ATCC PTA-5134 | 11 Apr. 2003 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Applicants have solved the stated problem by providing a process to prepare (E)- and (Z)-2-methyl-2-butenoic acids (2M2BA) in high yield and at high concentration in the reaction mixture starting from a mixture of (E,Z)-2-methyl-2-butenenitriles (2M2BN) and using a catalyst having either a nitrilase activity or a combination of nitrile hydratase and amidase activities. Applicants have isolated and characterized two new microbial catalysts, *C. testosteroni* S2B-1 (ATCC PTA-5135) and *C. testosteroni* S5C (ATCC PTA-5134), which have a combination of regioselective nitrile hydratase and amidase activities useful for converting the (E)-2M2BN component of (E,Z)-2M2BN to (E)-2M2BA, without concomitant hydrolysis of (Z)-2M2BN to (Z)-2M2BA.

The method regioselectively hydrolyzes (E)-2M2BN to (E)-2-methyl-2-butenoic acid (2M2BA). The method provides high yields without significant conversion of (Z)-2M2BN to (Z)-2M2BA. The regioselective hydrolysis of (E)-2M2BN to (E)-2M2BA makes possible the facile separation of (E)-2M2BA (as the ammonium salt) from (Z)-2M2BN or (Z)-2-methyl-2-butenamide (2M2BAm), and for the subsequent conversion of (Z)-2M2BN or (Z)-2M2BAm to (Z)2M2BA.

(E)- and (Z)-2M2BA are useful for preparing flavor and fragrance ingredients, as well as in for preparing pharmaceutical intermediates. The process has the added industrial advantages of low temperature and energy requirements and low waste or byproduct production relative to previously known chemical methods.

Microbial catalysts can hydrolyze a nitrile directly to the corresponding carboxylic acids using 1) a nitrilase (EC 3.5.5.7) enzyme without intermediate production of the corresponding amide (Equation 1), or 2) a combination of nitrile hydratase (EC 4.2.1.84) and amidase (EC 3.5.1.4) enzymes, in which case a nitrile hydratase (NHase) initially converts a nitrile to an amide, and then the amide is subsequently converted by the amidase to the corresponding carboxylic acid (Equation 2):

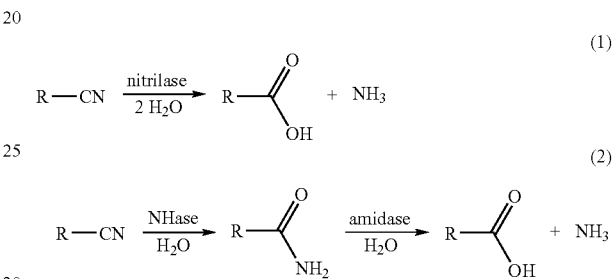

In the present invention, microbial catalysts having nitrilase activity, or a combination of nitrile hydratase and amidase activities, have been identified which can convert the (E)-2M2BN component of a mixture of (E,Z)-2M2BN with high regiospecificity to the corresponding carboxylic acid at high concentration and at complete conversion of the nitrile. The process gives no significant conversion of (Z)-2M2BN to (Z)-2M2BA. The identified catalysts of the present invention eliminate the need for close monitoring over the course of the reaction to maintain a low concentration of nitrile, and do not require the reaction be run at a low temperature (5-10° C.) to maintain the stability of the enzyme catalyst. Instead, the process uses either a thermally-stable nitrilase or a combination of thermostable nitrile hydratase and amidase enzymes as catalysts for the desired conversions.

U.S. Pat. No. 5,858,736 describes using the nitrilase activity of a microbe, *Acidovorax facilis* 72W (ATCC 55746), as a catalyst for the hydrolysis of aliphatic α,ω-dinitriles to the corresponding ω-cyanocarboxylic acids and ammonia in an aqueous reaction mixture. The nitrilase catalyzed the hydrolysis of an α-alkyl-α,ω-dinitrile to the ω-cyanocarboxylic acid resulting from hydrolysis of the ω-cyano group with at least 98% regioselectivity at 100% conversion. U.S. Pat. No. 5,814,508 describes a process whereby heating a suspension of *Acidovorax facilis* 72W (ATCC 55746) in a suitable buffer at 50° C. for a short period of time deactivates an undesirable nitrile hydratase and amidase activity of the whole-cell catalyst, without producing a significant decrease in the desired nitrilase activity.

The complete regioselectivity of the nitrilase catalysts of the present invention for hydrolysis of only (E)-2-methyl-2-butenenitrile to the corresponding carboxylic acid, with no detectable hydrolysis of (Z)-2-methyl-2-butenenitrile under the same reaction conditions, was unexpected and could not have been predicted. U.S. Pat. No. 5,858,736 describes the use of the nitrilase catalysts of the present invention for the hydrolysis of 2-methylglutaronitrile and 2-methyleneglutaronitrile to the corresponding ω-cyanocarboxylic acids; for the hydrolysis of 2-methylglutaronitrile, no 2-methyl4-cyanobutanoic acid was produced, and 2-methylglutaric acid was produced at <2% total yield at complete conversion of 2-methylglutaronitrile, whereas for hydrolysis of 2-methyleneglurarnonitrile, 4-cyano-4-pentenoic acid was the only hydrolysis product, and there was no hydrolysis of the cyano group vicinal to the α-methylene substituent.

In contrast, the accompanying examples demonstrate that the nitrilase catalysts described in U.S. Pat. No. 5,858,736 are capable of catalyzing the complete conversion of 2-methyl-3-butenenitrile, (cis)-2-pentenenitrile, and (trans)-2-pentenenitrile to the corresponding carboxylic acids. Neither the presence or absence of a methyl or methylene substituent at the a-position relative to a cyano group, nor the presence or absence of α,β-unsaturation relative to the position of a cyano group, could be used to predict if an α-alkyl substituted nitrile is a substrate for the nitrilase catalysts of the present invention. Similarly, it could not have been predicted whether or not the nitrile hydratase and amidase catalysts of the present invention would exhibit regioselectivity towards hydrolysis of geometric isomers of 2,3-disubstituted acrylonitriles such as (E)- and (Z)-2-methyl-2-butenenitrile.

It was also not previously known nor predicted before Applicants' invention that the regioselective nitrilase biocatalysts derived from *Acidovorax facilis* 72W would be stable to the high concentrations of (E,Z)-α,β-unsaturated nitrile and (E)-α,β-unsaturated carboxylic acid present over the course of a single reaction, or over the course of a series of reactions when the catalyst was recycled to produce (E)-2M2BA at high concentration. In particular, the nitrilase enzyme of the present invention relies on the sulfhydryl group of a cysteine in the active site of the enzyme for its catalytic activity (WO 0175077 A2), and α,β-unsaturated nitrites, amides and carboxylic acids are known to be highly reactive towards sulfhydryl groups, where a sulfhydryl group may react at the β-position of these compounds and thereby irreversibly inactivate the enzyme.

U.S. Pat. No. 5,858,736 also describes the use of a combination of a regioselective nitrile hydratase and amidase activities of *C. testosteroni* 5-MGAM-4D (ATCC 55744), as catalyst for the hydrolysis of aliphatic α,ω-dinitriles to the corresponding ω-cyanocarboxylic acids in an aqueous reaction mixture. This microbe exhibits both non-regioselective and regioselective nitrile hydratase activities, but heating a suspension of *C. testosteroni* 5-MGAM4D in a suitable buffer at 50° C. for a short period of time deactivates the undesirable non-regioselective nitrile hydratase of the microbial cell catalyst, without producing a significant decrease in the desired regioselective nitrile hydratase and amidase activities. In the present application, no heat-treatment of *C. testosteroni* 5-MGAM4D is required for regioselective hydrolysis of (E)-2M2BN to (E)-2M2BA, where there is no concomitant hydrolysis of (Z)-2M2BN to (Z)-2M2BA.

Microbial Catalysts

Applicants have isolated and characterized two new microbial catalysts, *C. testosteroni* S2B-1 (ATCC PTA-5135) and *C. testosteroni* S5C (ATCC PTA-5134), which have a combination of regioselective nitrile hydratase and amidase activities useful for converting the (E)-2M2BN component of (E,Z)-2M2BN to (E)-2M2BA, without concomitant hydrolysis of (Z)-2M2BN to (Z)-2M2BA.

In the present invention, the *C. testosteroni* catalysts utilize two enzyme activities to convert (E)-2M2BN to (E)-2M2BA. It was not previously known (and could not have been predicted) that both the regioselective nitrile hydratase and amidase enzymes would be stable to the high concentrations of α,β-unsaturated nitriles, amides, and carboxylic acids present over the course of a single reaction or over the course of a series of reactions when the catalyst was recycled to produce (E)-2M2BA at high concentration. All known amidase enzymes, including those of the present invention, rely on the sulfhydryl group of a cysteine in the active site of the enzyme for their catalytic activity, and α,β-unsaturated nitrites, amides, and carboxylic acids are known to be highly reactive towards sulfhydryl groups, where a sulfhydryl group may react at the β-position of the compounds and thereby irreversibly inactivate the enzyme.

Definitions:

In this disclosure, a number of terms and abbreviations are used. The following definitions apply unless specifically stated otherwise.

"Catalyst", "enzyme catalyst", or "microbial cell catalyst" refer to a catalyst expressing a nitrilase activity or a combination of nitrile hydratase and amidase activities. The catalyst may be in the form of an intact microbial cell, permeabilized microbial cell(s), one or more cell components of a microbial cell extract, partially-purified enzyme(s), or purified enzyme(s).

The term "thermally-stable" characterizes an enzyme that retains activity despite exposure to a given temperature.

The terms "*Comamonas testosteroni*" and "*C. testosteroni*" are used interchangeably.

The terms "*Acidovorax facilis*" and "*A. facilis*" are used interchangeably.

The terms "*Escherichia coli*" and "*E. coli*" are used interchangeably.

The term "(E)-2-methyl-2-butenenitrile" is synonymous with (E)-2-methylcrotononitrile, tiglonitrile, trans-2-methyl-2-butenenitrile, and all other synonyms of CAS Registry Number 30574-97-1.

The term "(Z)-2-methyl-2-butenenitrile" is synonymous with (Z)-2-methylcrotononitrile, angelonitrile, cis-2-methyl-2-butenenitrile, and all other synonyms of CAS Registry Number 20068-02-4.

The term "2-methyl-3-butenenitrile" is synonymous with 3-cyanobut-1-ene, and all other synonyms of CAS Registry Number 16529-56-9.

The term "(E)-2-methyl-2-butenoic acid" is synonymous with (E)-2-methylcrotonic acid, tiglic acid, (E)-α-methylcrotonic acid, (E)-2,3-dimethylacrylic acid, (E)-2-methylcrotonic acid, cevadic acid, tiglinic acid, trans-α,β-dimethylacrylic acid, trans-2,3-dimethylacrylic acid, trans-2-methyl-2-butenoic acid, trans-2-methylcrotonic acid, and all other synonyms of CAS Registry Number 80-59-1.

The term "(Z)-2-methyl-2-butenoic acid" is synonymous with (Z)2-methylcrotonic acid, angelic acid, (Z)-α-methylcrotonic acid, (Z)-2,3-dimethylacrylic acid, (Z)-2-methylcrotonic acid, cis-α,β-dimethylacrylic acid, cis-2,3-dimethylacrylic acid, cis-2-methyl-2-butenoic acid, cis-2-methylcrotonic acid, and all other synonyms of CAS Registry Number 565-63-9.

The term "(E)-2-methyl-2-butenamide" is synonymous with (E)-2-methylcrotonamide, tiglic acid amide, tiglamide, and all other synonyms of CAS Registry Number 6028-38-2.

The term "(Z)-2-methyl-2-butenamide" is synonymous with (Z)-2-methylcrotonamide, angelic acid amide, angelamide, and all other synonyms of CAS Registry Number 5953-75-3.

The term "suitable aqueous reaction mixture" refers to the materials and water in which the nitrile substrate and enzyme catalyst come into contact. Components of suitable aqueous reaction mixtures are referred to herein and those skilled in the art appreciate the range of component variations suitable for this process.

The abbreviations in the specification correspond to units of measure, techniques, properties, or compounds as follows: "sec" means second(s), "min" means minute(s), "h" means hour(s), "d" means day(s), "mL" means milliliters, "L" means liters, "mM" means millimolar, "M" means molar, "mmol" means millimole(s), and "wt" means weight. "HPLC" means high performance liquid chromatography, "ca" means approximately, "O.D." means optical density at the designated wavelength, "IU" means International Units.

Methods and Materials:

Growth of Acidovorax facilis strain 72W (ATCC 55746)

One frozen seed lot vial of Acidovorax facilis strain 72W (ATCC 55746) was thawed and the 1 mL contents placed in 500 mL of sterile Inoculum Medium listed below. The inoculum was grown at 30° C. with shaking at 250 rpm in a two L flask for 24-30 h.

Inoculum Medium

| Component: | Final Concentration: |
|---|---|
| Potassium phosphate, monobasic | 1.5 g/L |
| Potassium phosphate, dibasic | 3.4 g/L |
| Ammonium sulfate | 1.5 g/L |
| Trisodium citrate, dihydrate | 1 g/L |
| Magnesium sulfate, heptahydrate | 0.4 g/L |
| Trace metal solution (below) | 1 mL/L |
| Amberex 695 (Universal Foods) | 1 g/L |
| Glycerol (sterilized separately) | 8 g/L |

Trace Metal Solution

| Component: | Stock Concentration: |
|---|---|
| Hydrochloric Acid | 10 mL/L |
| Calcium chloride, dihydrate | 11.4 g/L |
| Manganese Sulfate, monohydrate | 1.23 g/L |
| Copper sulfate, pentahydrate | 0.63 g/L |
| Cobalt chloride, hexahydrate | 0.16 g/L |
| Boric Acid | 0.91 g/L |
| Zinc sulfate, heptahydrate | 1.77 g/L |
| Sodium molybdate, dihydrate | 0.05 g/L |
| Vanadyl sulfate, dihydrate | 0.08 g/L |
| Nickel nitrate, hexahydrate | 0.04 g/L |
| Sodium selenite | 0.04 g/L |
| Ferrous sulfate, heptahydrate | 6.00 g/L |

The inoculum from the shake flask was transferred aseptically to a pre-sterilized Braun Biostat C fermentor containing Fermentor Medium listed below. Growth occurred under the following conditions: 32° C., pH 6.8-7.0, dissolved oxygen at 25% of saturation. At inoculation the fermentor contained 8.5 L of Fermentor Medium plus 218 g of Nutrient Feed solution, giving a starting concentration of approximately 7 g/L glycerol. The Nutrient Feed solution includes the following components that were sterilized separately and combined after cooling: potassium phosphate, monobasic, 19.6 g in 0.25 L deionized water; magnesium sulfate, heptahydrate, 3.3 g, plus sulfuric acid, 4 mL, in 0.15 L deionized water; Trace Metal solution, 67 mL, plus 400 g glycerol in 0.80 L deionized water. At 18 h post inoculation, feeding of Nutrient Feed solution began. Initially, the Nutrient Feed solution was added at a rate of 0.4 g feed/minute (0.15 g glycerol/min). The culture OD 550 was approximately 8-9. At 26 h, the feed rate was increased to 0.9 g feed/minute (0.3 g glycerol/min). The OD 550 was approximately 16-18. A final increase in feed rate to 1.8 g feed/minute (0.6 g glycerol/min) was made at 34 h. This rate was maintained to the end of run (about 42 h). The final OD 550 was approximately 65-75.

Fermentor Medium

| Component: | Final Concentration: |
|---|---|
| Potassium phosphate, monobasic | 0.39 g/L |
| Potassium phosphate, dibasic | 0.39 g/L |
| Difco yeast extract | 5.0 g/L |

Cells, as wet cell paste, were recovered by centrifugation and stored frozen until use. Dry cell weight of wet cell paste, obtained by lyophilization, was typically 24% of wet cell weight. Acidovorax facilis 72W (ATCC 55746) cells were heated to 50° C. for 1 h in 0.35 M phosphate buffer (pH 7.0) to inactivate nitrile hydratase activity before use as a catalyst Two mutants of the Acidovorax facilis 72W (ATCC 55746) strain have been prepared (U.S. Pat. No. 5,858,736, incorporated by reference) which produce only very low levels of the nitrile hydratase activity of the parent strain. These nitrile hydratase-deficient mutant strains derived from A. facilis 72W (Acidovorax facilis 72-PF-15 (ATCC 55747) and Acidovorax facilis 72-PF-17 (ATCC 55745)), do not require heat-treatment of the cells prior to use as an enzyme catalyst for the hydrolysis of (E,Z)-2M2BN to a mixture of (E)-2M2BA and (Z)-2M2BN.

Preparation of Cell Extract and Purification of Nitrilase Protein

All steps in this procedure were performed at 5° C. and at pH 7.5 unless otherwise stated.

A 25 wt % suspension of Acidovorax facilis 72W (ATCC 55746) wet cell paste was prepared in 20 mM Tris buffer, pH 7.5, 0.1 mM phenylmethylsulfonyl fluoride (PMSF), and 2.0 mM dithiothreitol.

An extract of this suspension was prepared by passage through a French press (American Instrument Co., Silver Springs, Md., USA) according to methods known to the art. Following a centrifugation at 27,500×g for 30 min to remove cell debris, a 20-55% ammonium sulfate fractionation of the extract was prepared and then concentrated by overnight precipitation following the addition of solid ammonium sulfate to 65% of saturation. The concentrated protein precipitate was reconstituted using a minimum volume of 20 mM Tris, pH 7.5 (Buffer A) and desalted over a PD10 column containing Sephadex G-25 resin (Pharmacia, Milwaukee, Wis.). Following desalting, the concentrated protein extract was fractionated by anion exchange chromatography using a column containing 50 mL of Q-Sparse fast flow (Pharmacia). After loading the column with the concentrated protein extract, the column was washed with three column volumes of Buffer A at a flow rate of 2 mL/min to remove un-adsorbed protein. Adsorbed protein was eluted from the column using a 0-0.5 M NaCl gradient prepared in Buffer A. Elution of protein from the column was monitored at 280 nm.

Nitrilase activity was monitored throughout purification using an assay measuring the hydrolysis of benzonitrile to produce benzoic acid (Gavagan et al., *Appl. Microbiol. Biotechnol.*, 52:654-659 (1999)). Nitrilase activity eluted at 0.4 M NaCl. Protein components in the 0.4 M NaCl protein fraction were separated by gel electrophoresis (SDS-PAGE) performed under reducing conditions (5% β-mercaptoethanol) on a 10-15% SDS polyacrylamide gel. Greater than 50% of the 0.4 M NaCl protein fraction consisted of a protein with subunit molecular weight of 39.7 kd. Using methods known in the art, the native molecular weight of the nitrilase was determined to be 570 kd following gel filtration chromatography in 20 mM phosphate buffer at pH 7 using a Hiload 16/60 Superdex 200 column (Pharmacia) that had been calibrated using gel filtration MW standards (Pharmacia #17-0442-01). Following gel filtration, the nitrilase protein was >90% pure. The specific activity of the purified enzyme was determined to be 35 IU/mg protein using 2-methylglutaronitrile as substrate at 25° C.

Preparation of *Escherichia coli* SS1001 (ATCC PTA-1177) and *Escherichia coli* SW91 (ATCC PTA-1175)

The nitrilase gene (SEQ ID NO 1) of *Acidovorax facilis* 72W was cloned and sequenced, and over-expressed in *Escherichia coli* to produce two *E. coli* transformants, *E. coli* SS1001 (ATCC PTA-1177) and *E. coli* SW91 (ATCC PTA-1175). These procedures have been described in WO 0175077 A2 (equivalent to US PAT APP 2001/823373, which is incorporated by reference).

The nucleotide sequence (SEQ ID NO:3) and deduced amino acid sequence (SEQ ID NO:4) for the nitrilase expressed in *E. coli* SS1001 contains two minor nucleotide substitutions in comparison to wild type *Acidovorax facilis* 72W nitrilase sequence. First, the start codon is ATG instead of GTG to facilitate expression in *E. coli*. Second, a single nucleotide substitution at position 1098 was introduced during the cloning process, resulting in a corresponding amino acid change of proline (CCA) to serine (TCA) near the C-terminal end of the polypeptide (SEQ ID NOs:3 and 4).

Growth of *Comamonas testosteroni* 5-MGAM4D (ATCC 55744)

*Comamonas testosteroni* 5-MGAM4D (ATCC 55744) was enriched from soil collected in Orange, Tex., U.S.A., using standard enrichment procedures with E2 basal medium listed below (pH 7.2).

| E2 Basal Medium g/L | | | |
|---|---|---|---|
| $KH_2PO_4$ | 1.4 | $NaMoO_4.2H_2O$ | 0.0025 |
| $NaH_2PO_4$ | 6.9 | $NiCl_2.6H_2O$ | 0.01 |
| KCl | 0.5 | $CuSO_4.2H_2O$ | 0.005 |
| $MgSO_4.7H_2O$ | 0.5 | Biotin | 0.0002 |
| $CaCl_2$ | 0.025 | folic acid | 0.0002 |
| NaCl | 1 | pyridoxine.HCl | 0.001 |
| sodium citrate | 0.1 | Riboflavin | 0.0005 |
| $FeSO_4.7H_2O$ | 0.05 | nicotinic acid | 0.0005 |
| $CoCl_2.6H_2O$ | 0.01 | Pantothenic acid | 0.0005 |
| $MnCl_2.4H_2O$ | 0.001 | Vitamin B12 | 0.00001 |
| $ZnCl_2$ | 0.0005 | p-aminobenzoic acid | 0.0005 |
| $H_3BO_3$ | 0.000062 | | |

The table below contains modifications that were made to the E2 basal medium for the enrichment described above. Frozen 15% glycerol stocks were maintained at −65° C. to −70° C.

| Strain | Enrichment Nitrile | Other |
|---|---|---|
| *Comamonas testosteroni* 5-MGAM-4D | 0.2% 2-methylglutaramide | pH 5.6 |

*Comamonas testosteroni* 5-MGAM4D was grown aerobically under the following conditions for testing nitrile transformation activity.

| Strain | Nitrile/Amide | Medium | °C. | Time (h) |
|---|---|---|---|---|
| 5-MGAM-4D | 0.2% (w/v) propionamide | E2, 0.6% (w/v) glucose + $Na_2$succinate.$2H_2O$ | 30 | 29 |

Harvested cells were frozen at −65 to −70° C. until used for nitrile transformation.

Isolation, Growth, and Nitrile Hydrolysis Activity of *Comamonas testosteroni* S2B-1 (ATCC PTA-5135) and *Comamonas testosteroni* S5C (ATCC PTA-5134)

*Comamonas testosteroni* S2B-1 and *Comamonas testosteroni* S5C were isolated from extracts of soil collected in Orange, Tex., U.S.A., using standard enrichment procedures using S12-N medium. S12-N medium contains the following: $Na_2SO_4$, 10 mM; potassium phosphate buffer, pH 7.0, 50 mM; $MgCl_2$, 2 mM; $CaCl_2$, 0.7 mM; $MnCl_2$, 50 μM; $FeCl_3$, 1 μM; $ZnCl_3$, 1 μM; $CuSO_4$, 1.72 μM; $CoCl_2$, 2.53 μM; $Na_2MoO_2$, 2.42 μM; $FeSO_4$, 0.0001%; yeast extract, 0.001%; and thiamine hydrochloride, 2 μM. The enrichment culture was established by inoculating 10 μL of soil extract into 10 mL of S12-N medium in a 50 mL Erlenmeyer flask. The enrichment culture was supplemented with 100 ppm 3-hydroxyvaleronitrile (3-HVN) added directly to the culture medium and was incubated at 30° C. with reciprocal shaking. The enrichment culture was maintained by adding 100 ppm of 3-HVN every 2-3 days. The culture was diluted every 4-6 days by replacing 9 mL of the culture with the same volume of S12-N medium. Bacteria that utilize 3-HVN as a sole source of carbon, nitrogen, and energy or as a nitrogen source were isolated by spreading samples of the enrichment culture onto S12-N agar (S12-N medium with 1.5% Difco Noble Agar). 3-HVN (10 μL) was placed on the interior of each Petri dish lid. The Petri dishes were sealed with parafilm and incubated upside down at 28° C. Representative bacterial colonies were then single colony passaged several times on S12-N agar with 3-HVN supplied on the interior of each Petri dish lid. *Comamonas testosteroni* S2B-1 and *Comamonas testosteroni* S5C were among the strains isolated using this procedure.

*Comamonas testosteroni* S5C was grown in shake flask culture using E2 medium w/3-HVN as sole carbon and nitrogen source. The culture was incubated at 30° C. for 20 h with agitation set to 200 rpm.

*Comamonas testosteroni* S2B-1 was grown aerobically for 29 h in a 10 L fermentation. An inoculum was prepared by growth of a stock culture of either strain at 32° C. for 15 h in a 2.0 L unbaffled shake flask containing 500 mL of the medium described below in an incubator shaker set at an agitation rate of 300 rpm. At inoculation, the fermentor contained 8.5 L of Fermentor Medium. Dissolved oxygen was held at 25% of saturation, at 32° C., and pH at 6.8-7.0.

Fermentor Medium

| Component | Stock Concentration | Component | Stock Concentration |
|---|---|---|---|
| Fermentor Medium: | | | |
| Potassium phosphate, monobasic | 1.8 g/L | ammonium sulfate, | 4.5 g/L |
| Red Star yeast extract | 5.0 g/L | magnesium sulfate, heptahydrate | 0.9 g/L |
| DL-lactic acid, sodium salt | 15.0 g/L | | |
| Mazu DF204 antifoam | 1.0 mL/L | Trace metals (100X) | 18 mL/L |
| Trace Metal Solution: | (100X concentrate) | | |
| hydrochloric acid | 4-5 mL/L | zinc sulfate, heptahydrate | 0.039 g/L |
| calcium chloride, dihydrate | 1.5 g/L | sodium molybdate | 0.3 g/L |
| copper sulfate, pentahydrate | 0.38 g/L | nickel chloride, pentahydrate | 0.25 g/L |
| cobalt chloride, hexahydrate | 0.2 g/L | ferrous sulfate, heptahydrate | 5.0 g/L |
| sodium citrate | 10.0 g/L | manganese chloride, tetrahydrate | 0.3 g/L |

Harvested cells were frozen at −65 to −70° C. until used for nitrile transformation. The 10 L fermentation method described above was also used for the growth of *Comamonas testosteroni* 5-MGAM4D.

Whole cells of *Comamonas testosteroni* 5-MGAM4D, *Comamonas testosteroni* S2B-1, and *Comamonas testosteroni* S5C, respectively, were tested for nitrile hydratase and amidase activity using either 3-hydroxyvaleronitrile or 3-hydroxyvaleramide as substrate at a concentration of 0.5 M. A 50 mg (dry cell weight)/mL cell suspension was prepared in 0.10 M potassium phosphate buffer, pH 7.0. Into a 20-mL glass scintillation vial equipped with a magnetic stir bar was added 3.0 mL of an aqueous solution of either 0.667 M 3-HVA or 0.667 3-HVAm at 25° C. With stirring, 1.0 mL of the cell suspension at 25° C. was added. At 5, 10, and 15 min after the addition of the cell suspension, a 100 µL aliquot was removed from the reaction mixture, mixed with 20 µL of 6.0 N HCl, 100 µL of deionized water, and 200 µL of 0.20 M sodium butyrate (HPLC external standard). Following centrifugation, the supernatant was analyzed by HPLC for the rate of production of either 3-HVAm from 3-HVA or 3-HVA from 3-HVAm.

A unit of nitrile hydratase or amidase activity (IU) is equivalent to production of 1 micromole 3-HVAm or 3-HVA/min, respectively. The activity level is reported as units per gram of dry cell weight and is reported in the following table (Table 1).

TABLE 1

Nitrile Hydratase/Amidase Activity of *Comamonas testosteroni* S2B-1, *Comamonas testosteroni* S5C, and *Comamonas testosteroni* 5-MGAM-4D

| C. testosteroni Strain | Enzyme Activity (U/g dcw) | |
|---|---|---|
| | Nitrile Hydratase | Amidase |
| S5C | 2367 | 767 |
| S2B-1 | 4719 | 976 |
| 5-MGAM-4D | 7868 | 1360 |

Use of Nitrilase or Nitrile Hydratase/Amidase Biocatalysts for the Regioselective Hydrolysis of (E)-2-Methyl-2-butenenitrile to (E)-2-Methyl-2-butenoic acid in a mixture of (E,Z)-2-Methyl-2-butenenitriles Intact microbial cells having nitrilase or nitrile hydratase/amidase activities can be used as catalyst without any pretreatment, or the microbial cells may be permeabilized by methods familiar to those skilled in the art, e.g., treatment with toluene, detergents, or freeze thawing, to improve the rate of diffusion of materials into and out of the cells (H. Felix, *Anal. Biochem.*, 120:211-234 (1982)).

The microbial cell catalyst can be immobilized in a polymer matrix, including but not limited to alginate, carrageenan, polyvinyl alcohol, or polyacrylamide gel, or on a soluble or insoluble support, including but not limited to celite, ion exchange resins, and polymethylmethacrylate, to facilitate recovery and reuse of the catalyst. The enzyme activity or activities can also be isolated from the microbial cells and used directly as catalyst, or the enzyme activity or activities can be immobilized in a polymer matrix or on a soluble or insoluble support. Methods to immobilize cells in a polymer matrix or on a soluble or insoluble support have been widely reported, as have methods for the immobilization of partially-purified or purified enzymes, and are well known to those skilled in the art (see, for example, *Methods in Biotechnology, Vol. 1: Immobilization of Enzymes and Cells;* Gordon F. Bickerstaff, Editor; Humana Press, Totowa, N.J., USA; 1997).

Examples of specific enzymes useful in the present invention include, but are not limited to, the *Acidovorax facilis* 72W nitrilase (ATCC 55746; SEQ ID NOs:1 and 2) and transformants, such as *Escherichia coli* SS1001, expressing a modified version of the 72W nitrilase (SEQ ID NOs: 3 and 4). Additionally, a combination of nitrile hydratase and amidase activity is also useful in the present invention.

The concentration of enzyme catalyst in the reaction mixture depends on the catalyst's specific activity and is chosen to obtain the desired rate of reaction. When using unimmobilized intact or permeabilized microbial cells as enzyme catalyst, the wet cell weight (wcw) of the microbial cell catalyst in a reaction mixture typically ranges from 0.001 g to 0.200 g of wet cells per mL of total reaction volume, preferably from 0.002 g to 0.050 g of wet cells per mL. When using immobilized intact or permeabilized microbial cells as enzyme catalyst, the amount of the immobilized cell catalyst in a reaction mixture typically ranges from 0.001 g to 0.400 g of catalyst per mL of total reaction volume, preferably from 0.050 g to 0.250 g of immobilized cell catalyst per mL. Soluble or immobilized enzymes are employed as enzyme catalysts in amounts which vary with the specific activity of the enzyme catalyst, but are typically in the ranges of 0.001 g to 0.050 g of soluble enzyme per mL of total reaction volume, and 0.010 g to 0.200 g of immobilized enzyme per mL of total reaction volume (but not limited to these ranges). The specific activity of a nitrilase catalyst (IU/gram catalyst) is determined by measuring the rate of hydrolysis of (E)-2-methyl-2-butenenitrile to the corresponding carboxylic acid, and the specific activity of a nitrile hydratase/amidase catalyst is determined by measuring the rate of hydration of (E)-2-methyl-2-butenenitrile to the corresponding amide (for nitrile hydratase specific activity) and the rate of hydrolysis of (E)-2-methyl-2-butenamide to the corresponding carboxylic acid (for amidase specific activity) of a 0.14 M solution of the appropriate substrate at 25° C., using a known weight of the catalyst. An IU of enzyme activity is defined as the amount of enzyme activity required to convert one micromole of substrate to product per minute.

The method of the present invention is useful for converting (E)-2-methyl-2-butenenitrile to the corresponding carboxylic acid. The method of the present invention is also useful for converting (E)-2-methyl-2-butenenitrile in a mixture of (E,Z)-2-methyl-2-butenenitrile to the corresponding carboxylic acid, thereby allowing for the facile recovery of the carboxylic acid (as the ammonium salt) from the product mixture which additionally contains unreacted (Z)-2-methyl-2-butenenitrile (when a nitrilase catalyst is used) or unreacted (Z)-2-methyl-2-butenenitrile and (Z)-2-methyl-2-butenamide (when a nitrile hydratase/amidase catalyst is used).

For the biocatalytic conversion of (E)-2-methyl-2-butenenitrile to the corresponding carboxylic acid, an aqueous reaction mixture containing the nitrile is prepared by mixing (E)-2-methyl-2-butenenitrile, or (E,Z)-2-methyl-2-butenenitrile, with an aqueous suspension of the enzyme catalyst. (E)-2-Methyl-2-butenenitrile, (Z)-2-methyl-2-butenenitrile and (E,Z)-2-methyl-2-butenenitrile are only moderately water soluble, ca 1.1 wt % (0.14 M) in the reaction mixture at 22° C. Their solubility also depends on the temperature of the solution and the salt concentration in the aqueous phase; the optional inclusion of a buffer, or the production of the ammonium salt of a carboxylic acid are two possible sources of salt in a reaction mixture.

In the present application, producing a reaction product at a concentration greater than the solubility limit of the starting nitrile is accomplished using a reaction mixture that is initially composed of two phases: an aqueous phase (containing the enzyme catalyst and dissolved aliphatic or aromatic nitrile) and an organic phase (the undissolved nitrile, optionally dissolved in an organic solvent not miscible with the aqueous phase). As the reaction progresses, the nitrile dissolves into the aqueous phase, eventually yielding a product mixture which may be a single phase, depending on the solubility of the products (and remaining starting material, if any) in water, and on the presence or absence of an optional organic solvent not miscible with water. Examples of optional organic solvents added to a reaction mixture include, but are not limited to, toluene, methyl-t-butyl ether, dichloromethane, and methyl isobutyl ketone.

The amount of water present in the reaction mixture containing (E)-2-methyl-2-butenenitrile or (E,Z)-2-methyl-2-butenenitrile and an enzyme catalyst may be, at a minimum, only as much water as is sufficient to result in a) complete conversion of the nitrile to the corresponding carboxylic acid, and b) maintenance of the hydrolytic activity of the enzyme catalyst. The reaction may also be run by adding (E)-2-methyl-2-butenenitrile or (E,Z)-2-methyl-2-butenenitrile to the reaction mixture at a rate approximately equal to the enzymatic reaction rate, thereby maintaining a single-phase aqueous reaction mixture, thereby avoiding the potential problem of substrate inhibition of the enzyme at high starting material concentrations.

The concentration of carboxylic acid product in the reaction mixture (as the ammonium salt) may range from 1 mM to 7 M, preferably between 100 mM and 4 M, and most preferably between 1 M and 3 M. The (E)-2-methyl-2-butenenitrile or (E,Z)-2-methyl-2-butenenitrile may be added to a suitable reaction mixture in one portion, or may be added continuously as the nitrile is hydrolyzed to maintain a low concentration of the nitrile over the course of the reaction, thus limiting any potential inhibitory affects of the starting material or products on the enzyme catalyst activity.

The temperature of the reaction is chosen to optimize both the reaction rate and the stability of the enzyme catalyst activity. The temperature of the reaction may range from just above the freezing point of the reaction mixture (ca. 0° C.) to 70° C., with a preferred range of reaction temperature of from 5° C. to 45° C. Reactions using the enzyme catalyst may be run unbuffered in water, or in an aqueous reaction mixture containing a buffer (e.g., sodium or potassium phosphate), where the initial pH of the reaction is between 5.0 and 10.0, and preferably between 6.0 and 8.0. As the reaction proceeds, the pH of the reaction mixture may change due to the formation of an ammonium salt of (E)-2-methyl-2-butenoic acid by the hydrolysis of the nitrile functionality of (E)-2-methyl-2-butenenitrile. The reaction can be run to complete conversion of (E)-2-methyl-2-butenenitrile with no pH control, or in the presence of added buffer to control pH, or a suitable acid or base can be added over the course of the reaction to maintain the desired pH.

The (E)-2-methyl-2-butenoic acid obtained by reaction of a mixture of (E,Z)-2-methyl-2-butenenitrile with a nitrilase catalyst may be readily isolated by first separating any insoluble solid matter (including the enzyme catalyst) from the reaction mixture. (Z)-2-methyl-2-butenenitrile present in the resulting product mixture as a separate organic phase (if any) is separated from the aqueous phase containing (E)-2-methyl-2-butenoic acid (as the ammonium salt) and soluble (Z)-2-methyl-2-butenenitrile. The (Z)-2-methyl-2-butenenitrile present in the aqueous phase is then extracted with a suitable solvent selected from the group consisting of (but not limited to) toluene, heptane, methyl isobutyl ketone, dichloromethane or methyl-t-butyl ether; the ammonium salt of (E)-2-methyl-2-butenoic acid has negligible solubility in the chosen extraction solvent. The (E)-2-methyl-2-butenoic acid product is then isolated from the aqueous phase by procedures well known to those of ordinary skill. Such procedures include but are not limited to concentration, ion exchange, distillation, electrodialysis, extraction, and crystallization. The product may be isolated as the ammonium salt or (after acidification) as the corresponding carboxylic acid. The recovered (Z)-2-methyl-2-butenenitrile, free from any significant concentration of (E)-2-methyl-2-butenenitrile, is then converted to (Z)-2-methyl-2-butenoic acid by procedures well known to those skilled in the art, including those methods for the conversion of nitriles to carboxylic acids disclosed in the present application.

Similarly, the (E)-2-methyl-2-butenoic acid obtained by reaction of a mixture of (E,Z)-2-methyl-2-butenenitrile with a nitrile hydratase/amidase catalyst may be readily isolated by first separating any insoluble solid matter (including the enzyme catalyst) from the reaction mixture. (Z)-2-methyl-2-butenenitrile (present in the resulting product mixture as a separate organic phase, if any) is separated from the aqueous phase containing (E)-2-methyl-2-butenoic acid (as the ammonium salt), (Z)-2-methyl-2-butenamide (to the extent there is conversion of (Z)-2-methyl-2-butenenitrile, see the accompanying examples) and soluble (Z)-2-methyl-2-butenenitrile. The (Z)-2-methyl-2-butenenitrile and (Z)-2-methyl-2-butenamide present in the aqueous phase are then extracted with a suitable solvent selected from the group consisting of (but not limited to) toluene, heptane, methyl isobutyl ketone, dichloromethane or methyl-t-butyl ether; the ammonium salt of (E)-2-methyl-2-butenoic acid has negligible solubility in the chosen extraction solvent. The (E)-2-methyl-2-butenoic acid product is then isolated from the aqueous phase by procedures well known to those of ordinary skill. Such procedures include but are not limited to concentration, ion exchange, distillation, electrodialysis, extraction, and crystallization. The product may be isolated as the ammonium salt or (after acidification) as the corresponding carboxylic acid. The recovered (Z)-2-methyl-2-butenenitrile, and (Z)-2-methyl-2-butenamide (if any), free from any significant concentration of (E)-2-methyl-2-butenenitrile, is then converted to (Z)-2-methyl-2-butenoic acid by procedures well known to those skilled in the art, including those methods for the conversion of nitriles or amides to carboxylic acids disclosed in the present application.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

In the following Examples, the percent recovery of nitrile, and the percent yields of the corresponding amide and carboxylic acid products were based on the initial concentration of nitrile present in the reaction mixture, and were determined by HPLC using a refractive index detector. Analyses for carboxylic acids, amides, and nitriles described in the following examples were performed using a Supelco LC-18-DB column (15 cm×4.6 mm dia.) with precolumn at 25° C. and 10 mM acetic acid, 10 mM sodium acetate in 7.5% methanol in water as eluent at 1.5 mL/min.

Example 1

Hydrolysis of (E)-2-Methyl-2-Butenenitrile to (E)-2-Methyl-2-Butenoic acid by *E. coli* SS1001 Cells A 5.0 mL suspension of 0.500 g (wet cell paste) *E. coli* SS1001 cells (ATCC PTA-1177) in 50 mM potassium phosphate buffer (pH 7.0) was added to a mixture of 4.91 mL of 50 mM potassium phosphate buffer (pH 7.0) and 80.2 mg of (E)-2-methyl-2-butenenitrile (98.8 mM final concentration of (E)-2-methyl-2-butenenitrile), and the resulting suspension stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)-2-methyl-2-butenenitrile and (E)-2-methyl-2-butenoic acid. After 2.5 h, the conversion of (E)-2-methyl-2-butenenitrile was 100%, and the yield of (E)-2-methyl-2-butenoic acid was 98%; no (E)-2-methyl-2-butenamide was produced over the course of the reaction.

Example 2

Attempted Hydrolysis of (Z)-2-Methyl-2-Butenenitrile to (Z)-2-Methyl-2-Butenoic acid by *E. coli* SS1001 Cells (Comparative)

The procedure described in Example 1 was repeated, except that 79.2 mg of (Z)-2-methyl-2-butenenitrile (97.6 mM final concentration of (Z)-2-methyl-2-butenenitrile) was substituted for (E)-2-methyl-2-butenenitrile. After 3.0 h, the recovery of (Z)-2-methyl-2-butenenitrile was 100%, and there was no conversion to (Z)-2-methyl-2-butenoic acid (0% yield).

Example 3

Reaction of a 1:1 Mixture of (E)- and (Z)2-Methyl-2-Butenenitrile with *E. coli* SS1001 Cells A 5.0 mL suspension of 0.500 g (wet cell paste) *E. coli* SS1001 cells (ATCC PTA-1177) in 50 mM potassium phosphate buffer (pH 7.0) was added to a mixture containing 4.91 mL of 50 mM potassium phosphate buffer (pH 7.0), 38.4 mg of (E)-2-methyl-2-butenenitrile (47.4 mM final concentration of (E)-2-methyl-2-butenenitrile), and 37.7 mg of (Z)-2-methyl-2-butenenitrile (46.5 mM final concentration of (Z)-2-methyl-2-butenenitrile), and the resulting suspension stirred at 25° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 23 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 100% and 0%, respectively.

Example 4

Reaction of a 1:1 Mixture of (E)- and (Z)-2-Methyl-2-Butenenitrile with *E. coli* SS1001 Cells A 5.0 mL suspension of 0.500 g (wet cell paste) *E. coli* SS1001 cells (ATCC PTA-1177) in 50 mM potassium phosphate buffer (pH 7.0) was added to a mixture containing 4.80 mL of 50 mM potassium phosphate buffer (pH 7.0), 80.5 mg of (E)-2-methyl-2-butenenitrile (100 mM final concentration of (E)-2-methyl-2-butenenitrile), and 80.7 mg of (Z)-2-methyl-2-butenenitrile (100 mM final concentration of (Z)-2-methyl-2-butenenitrile), and the resulting suspension stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 6 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 99% and 0%, respectively.

Example 5

Isomerization 2-Methyl-3-Butenenitrile to a Mixture of (E)- and (Z)-2-Methyl-2-Butenenitrile A mixture of 50 g of 2-methyl-3-butenenitrile and 5 g of activity I basic alumina was heated with stirring at 85° C. After 18 h, the conversion of 2-methyl-3-butenenitrile to a mixture of (E)- and (Z)-2-methyl-2-butenenitriles was 100%. The mixture was cooled to ambient temperature and filtered to yield 49.1 g (98% isolated yield) of a mixture of (E)-2-methyl-2-butenenitrile (72 mole %) and (Z)-2-methyl-2-butenenitrile (28 mole %).

Example 6

Reaction of a 72:28 Mixture of (E)- and (Z)-2-Methyl-2-Butenenitriles with *E. coli* SS1001 Cells A 5.0 mL suspension of 0.500 g (wet cell paste) *E. coli* SS1001 cells (ATCC PTA-1177) in 50 mM potassium phosphate buffer (pH 7.0) was added to a mixture containing 4.90 mL of 50 mM potassium phosphate buffer (pH 7.0) and 81.8 mg of a 72:28 mixture of (E)- and (Z)-2-methyl-2-butenenitrile (101 mM final concentration), and the resulting suspension stirred at 25° C. After 6 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 96% and 0%, respectively.

Example 7

Immobilization of *E. coli* SS1001 Cells in Calcium Alginate

Into a 250-mL media bottle equipped with magnetic stir bar and containing 59.7 g of distilled, deionized water at 50° C. was slowly added 3.30 g of FMC BioPolymer Protanal® LF 10/60 alginate with rapid stirring. The mixture was heated to 75-80° C. with rapid stirring until the alginate was completely dissolved, and the resulting solution cooled to 25° C. in a water bath. To the alginate suspension was added 46.76 g of *E. coli* SS1001 wet cell paste (19% dry cell weight) and 10.24 mL of distilled water with stirring. The cell/alginate mixture was added dropwise by syringe to 640 mL of 0.20 M calcium acetate buffer (pH 7.0) at 25° C. with stirring. After stirring for 2 h, the buffer was decanted from the resulting beads, which were resuspended in 216 mL of 0.20 M calcium acetate buffer (pH 7.0) at 25° C. With stirring, 4.52 g of 25 wt % glutaraldehyde (GA) in water was added and the beads mixed for 1.0 h at 25° C. To the suspension was then added 18.1 g of 12.5 wt % polyethylenimine (PEI) (BASF Lupasol®) PR971 L, average molecular weight ca. 750,000) in water, and the beads mixed for an additional 1 h at 25° C. The crosslinked beads were then washed twice with 270 mL of 5 mM calcium acetate buffer (pH 7.0) at 25° C., and stored in an aqueous buffer containing 1.0 M ammonium acetate, 4 mM calcium acetate, and 10 mM ammonium bicarbonate (pH 7.1) at 5° C.

Example 8

Reaction of a 72:28 Mixture of (E)- and (Z)-2-Methyl-2-Butenenitriles (0.4 M) with Alginate-Immobilized *E. coli* SS1001 Cells Into a 50-mL jacketed reaction vessel equipped with an overhead stirrer (temperature-controlled at 35° C. with a recirculating temperature bath) was placed 1.0 g of GA/PEI-crosslinked *E. coli* SS1001 cell/alginate beads prepared as described in Example 7. To the reaction vessel was added 18.0 mL of distilled, deionized water, 0.2 mL of 0.20 M calcium acetate buffer (pH 7.0, 2.0 mM final calcium ion concentration in reaction mixture) and 0.798 mL (0.651 g) of a 72:28 mixture of (E)- and (Z)-2-methyl-2-butenenitrile (0.401 M total concentration), and the mixture stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 18 h, the conversions of (E)-2-methyl-2-butenenitrile and (Z)-2-methyl-2-butenenitrile were 99% and 0%, respectively, and the yields of (E)-2-methyl-2-butenoic acid and (Z)-2-methyl-2-butenoic acid were 99% and 0%, respectively.

Example 9

Reaction of a 72:28 Mixture of (E)- and (Z)-2-Methyl-2-Butenenitriles (1.0 M) with Alginate-Immobilized *E. coli* SS1001 Cells Into a 50-mL jacketed reaction vessel equipped with an overhead stirrer (temperature-controlled at 35° C. with a recirculating temperature bath) was placed 2.0 g of GA/PEI-crosslinked *E. coli* SS1001 cell/alginate beads prepared as described in Example 7. To the reaction vessel was added 15.8 mL of distilled, deionized water, 0.2 mL of 0.20 M calcium acetate buffer (pH 7.0, 2.0 mM final calcium ion concentration in reaction mixture) and 2.00 mL (1.636 g) of a 72:28 mixture of (E)- and (Z)-2-methyl-2-butenenitrile (1.01 M total concentration), and the mixture stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 18 h, the conversions of (E)2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 100% and 0%, respectively.

Example 10

Reaction of a 72:28 Mixture of (E)- and (Z)-2-Methyl-2-Butenenitriles (2.0 M) with Alginate-Immobilized *E. coli* SS1001 Cells Into a 50-mL jacketed reaction vessel equipped with an overhead stirrer (temperature-controlled at 35° C. with a recirculating temperature bath) was placed 4.0 g of GA/PEI-crosslinked *E. coli* SS1001 cell/alginate beads prepared as described in Example 7. To the reaction vessel was added 11.8 mL of distilled, deionized water, 0.2 mL of 0.20 M calcium acetate buffer (pH 7.0, 2.0 mM final calcium ion concentration in reaction mixture) and 4.01 mL (3.27 g) of a 72:28 mixture of (E)- and (Z)-2-methyl-2-butenenitrile (2.02 M total concentration), and the mixture stirred at 35° C. Samples (0.100 mL) were mixed with 0.900 mL of 60 mM N-ethylacetamide (HPLC external standard) in 1:1 acetonitrile:methanol, the resulting mixture was centrifuged, and the supernatant analyzed by HPLC for (E)- and (Z)-2-methyl-2-butenenitrile and (E)- and (Z)-2-methyl-2-butenoic acid. After 22 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 100% and 0%, respectively.

Example 11

Catalyst Recycle in Reactions of a 72:28 Mixture of (E)- and (Z)-2-Methyl-2-Butenenitriles (0.4 M) with Alginate-Immobilized E. coli SS1001 Cells Into a 50-mL jacketed reaction vessel equipped with an overhead stirrer (temperature-controlled at 35° C. with a recirculating temperature bath) was placed 4.0 g of GA/PEI-crosslinked E. coli SS1001 cell/alginate beads prepared as described in Example 7. To the reaction vessel was added 15.0 mL of distilled, deionized water, 0.2 mL of 0.20 M calcium acetate buffer (pH 7.0, 2.0 mM final calcium ion concentration in reaction mixture) and 0.802 mL (0.656 g) of a 72:28 mixture of (E)- and (Z)-2-methyl-2-butenenitrile (0.404 M total concentration), and the mixture stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 20 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 100% and 0%, respectively.

At the end of the reaction the product mixture was decanted from the catalyst beads, and an additional 15.1 mL of distilled, deionized water, 0.2 mL of 0.20 M calcium acetate buffer (pH 7.0, 2.0 mM final calcium ion concentration in reaction mixture) and 0.809 mL (0.662 g, 0.407 M) of a 72:28 mixture of (E)- and (Z)-2-methyl-2-butenenitrile was mixed with the immobilized-cell catalyst at 35° C. After 20 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 97% and 0%, respectively. At the completion of the second reaction with catalyst recycle, the final concentration of (E)-2-methyl-2-butenoic acid and (Z)-2-methyl-2-butenenitrile were 357 mM and 78.9 mM, respectively.

Example 12

Immobilization of A. facilis 72W Cells in Calcium-crosslinked Alginate

Into a 250-mL media bottle equipped with magnetic stir bar and containing 59.7 g of distilled, deionized water at 50° C. was slowly added 3.30 g of FMC BioPolymer Protanal® LF 10/60 alginate with rapid stirring. The mixture was heated to 75-80° C. with rapid stirring until the alginate was completely dissolved, and the resulting solution cooled to 25° C. in a water bath. To the alginate suspension was added 37.46 g of A. facilis 72W (ATCC 55746) wet cell paste (24% dry cell weight) and 19.54 mL of distilled water with stirring. The cell/alginate mixture was added dropwise by syringe to 640 mL of 0.20 M calcium acetate buffer (pH 7.0) at 25° C. with stirring. After stirring for 2 h, the buffer was decanted from the resulting beads, which were resuspended in 216 mL of 0.20 M calcium acetate buffer (pH 7.0) at 25° C. With stirring, 4.52 g of 25 wt % glutaraldehyde (GA) in water was added and the beads mixed for 1.0 h at 25° C. To the suspension was then added 18.1 g of 12.5 wt % polyethylenimine (PEI) (BASF Lupasol® PR971 L, average molecular weight ca. 750,000) in water, and the beads mixed for an additional 1 h at 25° C. The crosslinked beads were then washed twice with 270 mL of 5 mM calcium acetate buffer (pH 7.0) at 25° C., and stored in an aqueous buffer containing 1.0 M ammonium acetate, 4 mM calcium acetate and 10 mM ammonium bicarbonate (pH 7.1) at 5° C.

Example 13

Catalyst Recycle in Reaction of a 72:28 Mixture of (E)- and (Z)-2-Methyl-2-Butenenitriles (0.4 M) with Alginate-Immobilized A. facilis 72W Cells Into a 50-mL jacketed reaction vessel equipped with an overhead stirrer (temperature-controlled at 35° C. with a recirculating temperature bath) was placed 4.0 g of GA/PEI-crosslinked A. facilis 72W cell/alginate beads prepared as described in Example 12. To the reaction vessel was added 15.0 mL of distilled, deionized water, 0.2 mL of 0.20 M calcium acetate buffer (pH 7.0, 2.0 mM final calcium ion concentration in reaction mixture) and 0.796 mL (0.651 g) of a 72:28 mixture of (E)- and (Z)-2-methyl-2-butenenitrile (0.401 M total concentration), and the mixture stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 18 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 100% and 0%, respectively.

At the end of the reaction the product mixture was decanted from the catalyst beads, and an additional 15.0 mL of distilled, deionized water, 0.2 mL of 0.20 M calcium acetate buffer (pH 7.0, 2.0 mM final calcium ion concentration in reaction mixture) and 0.802 mL (0.657 g, 0.405 M) of a 72:28 mixture of (E)- and (Z)-2-methyl-2-butenenitrile was mixed with the immobilized-cell catalyst at 35° C. After 20 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 97% and 0%, respectively. At the completion of the second reaction with catalyst recycle, the final concentration of (E)-2-methyl-2-butenoic acid and (Z)-2-methyl-2-butenenitrile were 358 mM and 82.7 mM, respectively.

Example 14

Immobilization of E. coli SS1001 Cells in Carrageenan

Into a 250 mL media bottle equipped with magnetic stir bar and containing 54.6 g of water at 50° C. was slowly added 2.88 g of kappa-carrageenan (FMC RG300) with rapid stirring. The mixture was heated to 75-80° C. with rapid stirring until the carrageenan was completely dissolved, and the resulting solution cooled to 55-56° C. (gelling temperature ca. 52° C.) in a thermostated water bath. A suspension of 18.6 g of *E. coli* SS1001 wet cell paste (25.7% dry cell wt) in 19.7 g of 0.35 M sodium phosphate buffer (pH 7.3) was heated to 50° C. for 15 min, then added to the carrageenan solution at 55-56° C. with stirring. The cell/carrageenan mixture was immediately added slowly to 383 mL of soybean oil at 50° C. with stirring using an overhead stirrer. After cell/carrageenan droplets of the desired size were produced in the oil by controlling the stirring rate, the temperature of the oil was reduced to 40-42° C. to gel the droplets, and the oil decanted from the resulting beads. The beads were washed with 150 mL of 0.1 M potassium bicarbonate buffer (pH 7.0), then suspended in 182 mL of this same buffer, and 1.9 g of 25 wt % glutaraldehyde in water was added and the beads mixed for 1 h at 25° C. To the mixture was then added 7.6 g of 12.5 wt % polyethylenimine (BASF Lupasol PR971 L, average Mw ca. 750,000) in water, and the beads mixed for 1 h at 25° C. The beads were then washed twice with 0.30 M ammonium bicarbonate (pH 7.0), and stored in this same buffer at 5° C.

Example 15

Catalyst Recycle in Reaction of a 72:28 Mixture of (E)- and (Z)-2-Methyl-2-Butenenitriles (0.4 M) with Carrageenan-Immobilized *E. coli* SS1001 Cells Into a 50-mL jacketed reaction vessel equipped with an overhead stirrer (temperature-controlled at 35° C. with a recirculating temperature bath) was placed 4.0 g of GA/PEI-crosslinked *E. coli* SS1001 cell/carrageenan beads prepared as described in Example 14. To the reaction vessel was added 15.2 mL of distilled, deionized water and 0.797 mL (0.652 g) of a 72:28 mixture of (E)- and (Z)-2-methyl-2-butenenitrile (0.401 M total concentration), and the mixture stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)- and (Z)-2-methyl-2-butenenitrile and (E)- and (Z)-2-methyl-2-butenoic acid. After 18 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 96% and 0%, respectively.

At the end of the reaction the product mixture was decanted from the catalyst beads, and an additional 15.2 mL of distilled, deionized water and 0.802 mL (0.657 g, 0.405 M) of a 72:28 mixture of (E)- and (Z)-2-methyl-2-butenenitrile was mixed with the immobilized-cell catalyst at 35° C. After 20 h, the conversions of (E)-2-methyl-2-butenenitrile and (Z)-2-methyl-2-butenenitrile were 100% and 0%, respectively, and the yields of (E)-2-methyl-2-butenoic acid and (Z)-2-methyl-2-butenoic acid were 96% and 0%, respectively. At the completion of the second reaction with catalyst recycle, the final concentration of (E)-2-methyl-2-butenoic acid and (Z)-2-methyl-2-butenenitrile were 353 mM and 81.9 mM, respectively.

Example 16

Isomerization of (Z)-2-pentenitrile to a 78:22 Mixture of (Z)- and (E)-2-Pentenitriles A mixture of 402.7 g (4.96 mol) of (Z)-2-pentenitrile, 16.0 g (61.1 mMol) of triphenylphosphine, and 8.4 g (61.6 mmol) of zinc chloride (anhydrous) was heated at 70° C. for 22 h. The resulting mixture was cooled to ambient temperature, and the insoluble zinc chloride filtered from the mixture and the mixture vacuum distilled at 82° C. and 130 torr to separate the resulting mixture of (Z)- and (E)-2-pentenitriles from triphenylphosphine and soluble zinc chloride. The resulting distillate was analyzed by gas chromatography, and the ratio of (Z)- and (E)-2-pentenitriles was 78:22 (mole:mole).

Example 17

Reaction of a 78:22 Mixture of (Z)- and (E)-2-Pentenitriles with *E. coli* SS1001 Cells (Comparative)

A 5.0 mL suspension of 0.500 g (wet cell paste) *E. coli* SS1001 cells (ATCC PTA-1177) in 50 mM potassium phosphate buffer (pH 7.0) was added to a mixture containing 4.90 mL of 50 mM potassium phosphate buffer (pH 7.0) and 81.8 mg of a 78:22 mixture of (Z)- and (E)-2-pentenitriles (101 mM final concentration), and the resulting suspension stirred at 35° C. After 4 h, the conversions of (Z)-2-pentenitrile and (E)-2-2-pentenitrile were 100% and 100%, respectively, and the yields of (Z)-2-pentenoic acid and (E)-2-pentenenoic acid were 100% and 100%, respectively.

Example 18

Hydrolysis of 2-Methyl-3-Butenenitrile to 2-Methyl-3-Butenoic acid by *E. coli* SS1001 Cells A 5.0 mL suspension of 0.500 g (wet cell paste) *E. coli* SS1001 cells (ATCC PTA-1177) in 50 mM potassium phosphate buffer (pH 7.0) was added to a mixture of 4.91 mL of 50 mM potassium phosphate buffer (pH 7.0) and 81.8 mg of 2-methyl-3-butenenitrile (101 mM final concentration), and the resulting suspension stirred at 35° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for 2-methyl-3-butenenitrile and 2-methyl-3-butenoic acid. After 1 h, the conversion of 2-methyl-3-butenenitrile was 100%, and 2-methyl-3-butenoic acid was the only product produced over the course of the reaction.

Example 19

Hydrolysis of (E)-2-Methyl-2-Butenenitrile to (E)-2-Methyl-2-Butenoic Acid by *C. testosteroni* S2B-1 Cells A 5.0 mL suspension of 0.500 g (wet cell paste) *C. testosteroni* S2B-1 cells (ATCC PTA-5135) in 50 mM potassium phosphate buffer (pH 7.0) was added to a mixture of 4.91 mL of 50 mM potassium phosphate buffer (pH 7.0) and 82.1 mg of (E)-2-methyl-2-butenenitrile (101 mM final concentration of (E)-2-methyl-2-butenenitrile), and the resulting suspension stirred at 25° C. Samples (0.100 mL)

were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)-2-methyl-2-butenenitrile and (E)-2-methyl-2-butenoic acid. After 1.5 h, the conversion of (E)-2-methyl-2-butenenitrile was 100%, and the yield of (E)-2-methyl-2-butenoic acid was 99%; no (E)-2-methyl-2-butenamide was observed over the course of the reaction.

Example 20

Hydrolysis of (Z)-2-Methyl-2-Butenenitrile to (Z)-2-Methyl-2-Butenoic Acid by *C. testosteroni* S2B-1 Cells (Comparative)

The procedure described in Example 19 was repeated, except that 80.6 mg of (Z)-2-methyl-2-butenenitrile (99.3 mM final concentration of (Z)-2-methyl-2-butenenitrile) was substituted for (E)-2-methyl-2-butenenitrile, and the reaction contained 10 mg *C. testosteroni* S2B-1 cells (wet cell wt.)/mL. After 1.5 h, the recovery of (Z)-2-methyl-2-butenenitrile was 92%, and a 8.4% yield of (Z)-2-methyl-2-butenamide was obtained; there was no conversion to (Z)-2-methyl-2-butenoic acid (0% yield). After 19 h, the recovery of (Z)-2-methyl-2-butenenitrile was 5.6%, and the yields of (Z)-2-methyl-2-butenenamide and (Z)-2-methyl-2-butenoic acid were 88% and 1.9%, respectively. After 47 h, there was 100% conversion of (Z)-2-methyl-2-butenenitrile, and the yields of (Z)-2-methyl-2-butenenamide and (Z)-2-methyl-2-butenoic acid were 91% and 3.7%, respectively Example 21

Reaction of a 72:28 Mixture of (E)- and (Z)-2-Methyl-2-Butenenitriles with *C. testosteroni* S2B-1 Cells A 5.0 mL suspension of 0.100 g (wet cell paste) *C. testosteroni* S2B-1 cells in 50 mM potassium phosphate buffer (pH 7.0) was added to a mixture containing 4.90 mL of 50 mM potassium phosphate buffer (pH 7.0) and 84.1 mg of a 72:28 mixture of (E)- and (Z)-2-methyl-2-butenenitrile (104 mM final concentration), and the resulting suspension stirred at 25° C. After 21 h, the conversions of (E)-2-methyl-2-butenenitrile and (Z)-2-methyl-2-butenenitrile were 100% and 17%, respectively; the yields of (E)-2-methyl-2-butenamide and (Z)-2-methyl-2-butenamide were 0% and 1.2%, respectively, and the yields of (E)-2-methyl-2-butenoic acid and (Z)-2-methyl-2-butenoic acid were 89% and 0%, respectively. After 47 h, the conversions of (E)-2-methyl-2-butenenitrile and (Z)-2-methyl-2-butenenitrile were 100% and 96%, respectively; the yields of (E)-2-methyl-2-butenamide and (Z)-2-methyl-2-butenamide were 0% and 87%, respectively, and the yields of (E)-2-methyl-2-butenoic acid and (Z)-2-methyl-2-butenoic acid were 100% and 0%, respectively.

Example 22

Hydrolysis of (E)-2-Methyl-2-Butenenitrile to (E)-2-Methyl-2-Butenoic acid by *C. testosteroni* S5C Cells A 5.0 mL suspension of 0.050 g (wet cell paste) *C. testosteroni* S5C cells (ATCC PTA-5134) in 50 mM potassium phosphate buffer (pH 7.0) was added to a mixture of 4.91 mL of 50 mM potassium phosphate buffer (pH 7.0) and 81.2 mg of (E)-2-methyl-2-butenenitrile (100 mM final concentration of (E)-2-methyl-2-butenenitrile), and the resulting suspension stirred at 25° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)-2-methyl-2-butenenitrile and (E)-2-methyl-2-butenoic acid. After 2.5 h, the conversion of (E)-2-methyl-2-butenenitrile was 100%, and the yield of (E)-2-methyl-2-butenoic acid was 99%; no (E)-2-methyl-2-butenamide was observed over the course of the reaction.

Example 23

Hydrolysis of (Z)-2-Methyl-2-Butenenitrile to (Z)-2-Methyl-2-Butenoic acid by *C. testosteroni* S5C Cells (Comparative)

The procedure described in Example 22 was repeated, except that 80.6 mg of (Z)-2-methyl-2-butenenitrile (99.4 mM final concentration of (Z)-2-methyl-2-butenenitrile) was substituted for (E)-2-methyl-2-butenenitrile. After 2.5 h, the recovery of (Z)-2-methyl-2-butenenitrile was 75%, and a 23% yield of (Z)-2-methyl-2-butenenamide was obtained; there was no conversion to (Z)-2-methyl-2-butenoic acid (0% yield). After 19 h, the recovery of (Z)-2-methyl-2-butenenitrile was 0.7%, and the yields of (Z)-2-methyl-2-butenenamide and (Z)-2-methyl-2-butenoic acid were 93% and 0%, respectively. After 47 h, there was 100% conversion of (Z)-2-methyl-2-butenenitrile, and the yields of (Z)-2-methyl-2-butenenamide and (Z)-2-methyl-2-butenoic acid were 91% and 3.9%, respectively.

Example 24

Hydrolysis of (E)-2-Methyl-2-Butenenitrile to (E)-2-Methyl-2-Butenoic acid by *C. testosteroni* 5-MGAM-4D Cells A 5.0 mL suspension of 0.250 g (wet cell paste) *C. testosteroni* 5-MGAM-4D cells (ATCC 55744) in 50 mM potassium phosphate buffer (pH 7.0) was added to a mixture of 4.91 mL of 50 mM potassium phosphate buffer (pH 7.0) and 81.6 mg of (E)-2-methyl-2-butenenitrile (101 mM final concentration of (E)-2-methyl-2-butenenitrile), and the resulting suspension stirred at 25° C. Samples (0.100 mL) were mixed with 0.900 mL of 60 mM N-ethylacetamide (HPLC external standard) in 1:1 acetonitrile:methanol, the resulting mixture was mixed, centrifuged, and the supernatant analyzed by HPLC for (E)-2-methyl-2-butenenitrile and (E)-2-methyl-2-butenoic acid. After 15 min, the conversion of (E)-2-methyl-2-butenenitrile was 100%, and the yield of (E)-2-methyl-2-butenoic acid was 100%; no (E)-2-methyl-2-butenamide was observed over the course of the reaction.

Example 25

Hydrolysis of (Z)-2-Methyl-2-Butenenitrile to (Z)-2-Methyl-2-Butenoic acid by *C. testosteroni* 5-MGAM-4D Cells (Comparative)

The procedure described in Example 24 was repeated, except that 80.0 mg of (Z)-2-methyl-2-butenenitrile (98.6 mM final concentration of (Z)-2-methyl-2-butenenitrile) was substituted for (E)-2-methyl-2-butenenitrile. After 30 min, the recovery of (Z)-2-methyl-2-butenenitrile was 53%, and a 47% yield of (Z)-2-methyl-2-butenenamide was obtained; there was no conversion to (Z)-2-methyl-2-butenoic acid (0% yield). After 175 min, the conversion of (Z)-2-methyl-2-butenenitrile was 100%, and the yields of (Z)-2-methyl-2-butenenamide and (Z)-2-methyl-2-butenoic acid were 99% and 1.2%, respectively. After 22.5 h, there was 100% conversion of (Z)-2-methyl-2-butenenitrile, and the yields of (Z)-2-methyl-2-butenenamide and (Z)-2-methyl-2-butenoic acid were 89% and 11%, respectively.

Example 26

Preparation of (E)- and (Z)-2-methyl-2-butenoic Acids by Enzymatic Hydrolysis of a 72:28 Mixture of (E)- and (Z)-2-Methyl-2-Butenenitriles A product mixture produced according to the method described in Example 10, containing ca. 1.44 M (E)-2-methyl-2-butenoic acid and ca. 0.56 M (Z)-2-methyl-2-butenenitrile, is decanted from the immobilized cell catalyst. The resulting product mixture is comprised of an aqueous layer containing the ammonium salt of (E)-2-methyl-2-butenoic acid and ca. 1.1 wt % (Z)-2-methyl-2-butenenitrile, and a second organic layer which is solely (Z)-2-methyl-2-butenenitrile. The (Z)-2-methyl-2-butenenitrile is separated from the aqueous phase, and the aqueous phase is extracted three times with an equivalent volume of methyl-t-butyl ether to remove the remaining (Z)-2-methyl-2-butenenitrile.

The pH of the aqueous phase is then adjusted to 2.0 with concentrated hydrochloric acid, and the (E)-2-methyl-2-butenoic acid extracted from the resulting aqueous mixture with methyl-t-butyl ether. The organic extracts are combined, dried over magnesium sulfate, filtered, and the methyl-t-butyl ether removed from the filtrate by distillation under reduced pressure to give (E)-2-methyl-2-butenoic acid in high yield and purity; the (E)-2-methyl-2-butenoic acid is further purified (if desired) by crystallization from ethyl acetate/hexanes.

The unreacted (Z)-2-methyl-2-butenenitrile recovered from the product mixture is mixed at 10 wt % with 6.0 N sulfuric acid and heated to 100° C. with stirring until complete conversion of (Z)-2-methyl-2-butenenitrile to (Z)-2-methyl-2-butenoic acid is achieved. The (Z)-2-methyl-2-butenoic acid is extracted from the resulting aqueous mixture with methyl-t-butyl ether. The organic extracts are combined, dried over magnesium sulfate, filtered, and the methyl-t-butyl ether is removed from the filtrate by distillation under reduced pressure to give (Z)-2-methyl-2-butenoic acid in high yield and purity. The (Z)-2-methyl-2-butenoic acid is further purified (if desired) by crystallization from ethyl acetate/hexanes.

What is claimed is:

1. A purified *Comamonas testosteroni* strain S2B-1 having regioselective nitrile hydratase and amidase activity and designated ATCC PTA-5135.

2. A purified *Comamonas testosteroni* strain S5C having regioselective nitrile hydratase and amidase activity and designated ATCC PTA-5134.

* * * * *

SEQUENCE LISTING

```
<160> NUMBER OF SEQ ID NOS: 10

<210> SEQ ID NO 1
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 1 gtg gtt tcg tat aac agc aag ttc ctc gcg gca acc gtt cag gca gag         48
Val Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc         96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa        144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag        192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta        240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa        288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
        115                 120                 125
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| cgc   | aag   | ctg   | aag   | ccc   | aca   | cac   | gtt   | gag   | cgt   | acg   | atc   | tac   | ggc   | gaa   | ggc   | 432  |
| Arg   | Lys   | Leu   | Lys   | Pro   | Thr   | His   | Val   | Glu   | Arg   | Thr   | Ile   | Tyr   | Gly   | Glu   | Gly   |      |
|       | 130   |       |       |       | 135   |       |       |       |       | 140   |       |       |       |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| aac   | gga   | acc   | gat   | ttc   | ctc   | acg   | cac   | gac   | ttc   | gcg   | ttc   | gga   | cgc   | gtc   | ggt   | 480  |
| Asn   | Gly   | Thr   | Asp   | Phe   | Leu   | Thr   | His   | Asp   | Phe   | Ala   | Phe   | Gly   | Arg   | Val   | Gly   |      |
| 145   |       |       |       |       | 150   |       |       |       |       | 155   |       |       |       |       | 160   |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gga   | ttg   | aac   | tgc   | tgg   | gaa   | cat   | ttc   | caa   | ccg   | ctc   | agc   | aag   | ttc   | atg   | atg   | 528  |
| Gly   | Leu   | Asn   | Cys   | Trp   | Glu   | His   | Phe   | Gln   | Pro   | Leu   | Ser   | Lys   | Phe   | Met   | Met   |      |
|       |       |       |       | 165   |       |       |       |       | 170   |       |       |       |       | 175   |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| tac   | agc   | ctc   | ggt   | gag   | cag   | gtc   | cac   | gtt   | gca   | tcg   | tgg   | ccg   | gcg   | atg   | tcc   | 576  |
| Tyr   | Ser   | Leu   | Gly   | Glu   | Gln   | Val   | His   | Val   | Ala   | Ser   | Trp   | Pro   | Ala   | Met   | Ser   |      |
|       |       |       | 180   |       |       |       |       | 185   |       |       |       |       | 190   |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| cct   | ctt   | cag   | ccg   | gat   | gtt   | ttc   | caa   | ctg   | agc   | atc   | gaa   | gcc   | aac   | gcg   | acg   | 624  |
| Pro   | Leu   | Gln   | Pro   | Asp   | Val   | Phe   | Gln   | Leu   | Ser   | Ile   | Glu   | Ala   | Asn   | Ala   | Thr   |      |
|       |       | 195   |       |       |       |       | 200   |       |       |       |       | 205   |       |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gtc   | acc   | cgc   | tcg   | tac   | gca   | atc   | gaa   | ggc   | caa   | acc   | ttt   | gtg   | ctt   | tgc   | tcg   | 672  |
| Val   | Thr   | Arg   | Ser   | Tyr   | Ala   | Ile   | Glu   | Gly   | Gln   | Thr   | Phe   | Val   | Leu   | Cys   | Ser   |      |
|       |       | 210   |       |       |       |       | 215   |       |       |       |       | 220   |       |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| acg   | cag   | gtg   | atc   | gga   | cct   | agc   | gcg   | atc   | gaa   | acg   | ttc   | tgc   | ctc   | aac   | gac   | 720  |
| Thr   | Gln   | Val   | Ile   | Gly   | Pro   | Ser   | Ala   | Ile   | Glu   | Thr   | Phe   | Cys   | Leu   | Asn   | Asp   |      |
| 225   |       |       |       |       | 230   |       |       |       |       | 235   |       |       |       |       | 240   |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gaa   | cag   | cgc   | gca   | ctg   | ttg   | ccg   | caa   | gga   | tgt   | ggc   | tgg   | gcg   | cgc   | att   | tac   | 768  |
| Glu   | Gln   | Arg   | Ala   | Leu   | Leu   | Pro   | Gln   | Gly   | Cys   | Gly   | Trp   | Ala   | Arg   | Ile   | Tyr   |      |
|       |       |       |       | 245   |       |       |       |       | 250   |       |       |       |       | 255   |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| ggc   | ccg   | gat   | gga   | agc   | gag   | ctt   | gcg   | aag   | cct   | ctg   | gcg   | gaa   | gat   | gct   | gag   | 816  |
| Gly   | Pro   | Asp   | Gly   | Ser   | Glu   | Leu   | Ala   | Lys   | Pro   | Leu   | Ala   | Glu   | Asp   | Ala   | Glu   |      |
|       |       || 260   |       |       |       |       | 265   |       |       |       |       | 270   |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| ggg   | atc   | ttg   | tac   | gca   | gag   | atc   | gat   | ctg   | gag   | cag   | att   | ctg   | ctg   | gcg   | aag   | 864  |
| Gly   | Ile   | Leu   | Tyr   | Ala   | Glu   | Ile   | Asp   | Leu   | Glu   | Gln   | Ile   | Leu   | Leu   | Ala   | Lys   |      |
|       |       |       | 275   |       |       |       |       | 280   |       |       |       |       | 285   |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gct   | gga   | gcc   | gat   | ccg   | gtc   | ggg   | cac   | tat   | tcg   | cgg   | cct   | gac   | gtg   | ctg   | tcg   | 912  |
| Ala   | Gly   | Ala   | Asp   | Pro   | Val   | Gly   | His   | Tyr   | Ser   | Arg   | Pro   | Asp   | Val   | Leu   | Ser   |      |
|       | 290   |       |       |       |       | 295   |       |       |       |       | 300   |       |       |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gtc   | cag   | ttc   | gac   | ccg   | cgc   | aat   | cat   | acg   | cca   | gtt   | cat   | cgc   | atc   | ggc   | att   | 960  |
| Val   | Gln   | Phe   | Asp   | Pro   | Arg   | Asn   | His   | Thr   | Pro   | Val   | His   | Arg   | Ile   | Gly   | Ile   |      |
| 305   |       |       |       |       | 310   |       |       |       |       | 315   |       |       |       |       | 320   |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| gac   | ggt   | cgc   | ttg   | gat   | gtg   | aat   | acc   | cgc   | agt   | cgc   | gtg   | gag   | aat   | ttc   | cga   | 1008 |
| Asp   | Gly   | Arg   | Leu   | Asp   | Val   | Asn   | Thr   | Arg   | Ser   | Arg   | Val   | Glu   | Asn   | Phe   | Arg   |      |
|       |       |       |       | 325   |       |       |       |       | 330   |       |       |       |       | 335   |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| ctg   | cga   | caa   | gcg   | gct   | gag   | cag   | gag   | cgt   | cag   | gca   | tcc   | aag   | cgg   | ctc   | gga   | 1056 |
| Leu   | Arg   | Gln   | Ala   | Ala   | Glu   | Gln   | Glu   | Arg   | Gln   | Ala   | Ser   | Lys   | Arg   | Leu   | Gly   |      |
|       |       |       | 340   |       |       |       |       | 345   |       |       |       |       | 350   |       |       |      |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| acg   | aaa   | ctc   | ttt   | gaa   | caa   | tcc   | ctt   | ctg   | gct   | gaa   | gaa   | ccg   | gtc   | cca   | gca   | 1104 |
| Thr   | Lys   | Leu   | Phe   | Glu   | Gln   | Ser   | Leu   | Leu   | Ala   | Glu   | Glu   | Pro   | Val   | Pro   | Ala   |      |
|       | 355   |       |       |       |       | 360   |       |       |       |       | 365   |       |       |       |       |      |

|     |     |      |
|-----|-----|------|
| aag | tag | 1110 |
| Lys |     |      |

<210> SEQ ID NO 2
<211> LENGTH: 369
<212> TYPE: PRT
<213> ORGANISM: Acidovorax facilis 72W

<400> SEQUENCE: 2

| | | | | | | | | | | | | | | |
|---|---|---|---|---|---|---|---|---|---|---|---|---|---|---|
| Val | Val | Ser | Tyr | Asn | Ser | Lys | Phe | Leu | Ala | Ala | Thr | Val | Gln | Ala | Glu |
| 1 | | | | 5 | | | | | 10 | | | | | 15 | |

| | | | | | | | | | | | | | | |
|---|---|---|---|---|---|---|---|---|---|---|---|---|---|---|
| Pro | Val | Trp | Leu | Asp | Ala | Asp | Ala | Thr | Ile | Asp | Lys | Ser | Ile | Gly | Ile |
| | | | 20 | | | | | 25 | | | | | 30 | | |

| | | | | | | | | | | | | | | |
|---|---|---|---|---|---|---|---|---|---|---|---|---|---|---|
| Ile | Glu | Glu | Ala | Ala | Gln | Lys | Gly | Ala | Ser | Leu | Ile | Ala | Phe | Pro | Glu |
| | | 35 | | | | | 40 | | | | | 45 | | | |

```
Val Phe Ile Pro Gly Tyr Pro Tyr Trp Ala Trp Leu Gly Asp Val Lys
 50                  55                  60
Tyr Ser Leu Ser Phe Thr Ser Arg Tyr His Glu Asn Ser Leu Glu Leu
 65                  70                  75                  80
Gly Asp Asp Arg Met Arg Arg Leu Gln Leu Ala Ala Arg Arg Asn Lys
                 85                  90                  95
Ile Ala Leu Val Met Gly Tyr Ser Glu Arg Glu Ala Gly Ser Arg Tyr
                100                 105                 110
Leu Ser Gln Val Phe Ile Asp Glu Arg Gly Glu Ile Val Ala Asn Arg
                115                 120                 125
Arg Lys Leu Lys Pro Thr His Val Glu Arg Thr Ile Tyr Gly Glu Gly
            130                 135                 140
Asn Gly Thr Asp Phe Leu Thr His Asp Phe Ala Phe Gly Arg Val Gly
145                 150                 155                 160
Gly Leu Asn Cys Trp Glu His Phe Gln Pro Leu Ser Lys Phe Met Met
                165                 170                 175
Tyr Ser Leu Gly Glu Gln Val His Val Ala Ser Trp Pro Ala Met Ser
                180                 185                 190
Pro Leu Gln Pro Asp Val Phe Gln Leu Ser Ile Glu Ala Asn Ala Thr
            195                 200                 205
Val Thr Arg Ser Tyr Ala Ile Glu Gly Gln Thr Phe Val Leu Cys Ser
210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
                260                 265                 270
Gly Ile Leu Tyr Ala Glu Ile Asp Leu Glu Gln Ile Leu Leu Ala Lys
            275                 280                 285
Ala Gly Ala Asp Pro Val Gly His Tyr Ser Arg Pro Asp Val Leu Ser
            290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
                340                 345                 350
Thr Lys Leu Phe Glu Gln Ser Leu Leu Ala Glu Glu Pro Val Pro Ala
            355                 360                 365
Lys

<210> SEQ ID NO 3
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 3 atg gtt tcg tat aac agc aag ttc ctc gcg gca acc gtt cag gca gag      48
Met Val Ser Tyr Asn Ser Lys Phe Leu Ala Ala Thr Val Gln Ala Glu
 1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
                20                  25                  30
```

```
atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
         35                  40                  45 gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                     85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
                100                 105                 110 ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
            115                 120                 125 cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
        130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
                180                 185                 190 cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
            195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
        210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
                260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
                340                 345                 350
```

```
acg aaa ctc ttt gaa caa tcc ctt ctg gct gaa gaa ccg gtc tca gca    1104
Thr Lys Leu Phe Glu Gln Ser Leu Leu Ala Glu Glu Pro Val Ser Ala
        355                 360                 365 aag tag                                                             1110
Lys

<210> SEQ ID NO 4
<211> LENGTH: 369
<212> TYPE: PRT
<213> ORGANISM: Acidovorax facilis 72W

<400> SEQUENCE: 4

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
```

```
                         340            345            350
         Thr Lys Leu Phe Glu Gln Ser Leu Leu Ala Glu Glu Pro Val Ser Ala
                 355                360                365
         Lys

<210> SEQ ID NO 5
<211> LENGTH: 633
<212> TYPE: DNA
<213> ORGANISM: Comamonas testosteroni 5-MGAM-4D
<220> FEATURE:
<221> NAME/KEY: CDS
<222> LOCATION: (1)..(633)

<400> SEQUENCE: 5 atg ggg caa tca cac acg cat gac cac cat cac gac ggg tac cag gca    48
Met Gly Gln Ser His Thr His Asp His His His Asp Gly Tyr Gln Ala
1               5                   10                  15 ccg ccc gaa gac atc gcg ctg cgg gtc aag gcc ttg gag tct ctg ctg    96
Pro Pro Glu Asp Ile Ala Leu Arg Val Lys Ala Leu Glu Ser Leu Leu
            20                  25                  30 atc gag aaa ggt ctt gtc gac cca gcg gcc atg gac ttg gtc gtc caa   144
Ile Glu Lys Gly Leu Val Asp Pro Ala Ala Met Asp Leu Val Val Gln
        35                  40                  45 acg tat gaa cac aag gta ggc ccc cga aac ggc gcc aaa gtc gtg gcc   192
Thr Tyr Glu His Lys Val Gly Pro Arg Asn Gly Ala Lys Val Val Ala
    50                  55                  60 aag gcc tgg gtg gac cct gcc tac aag gcc cgt ctg ctg gca gac ggc   240
Lys Ala Trp Val Asp Pro Ala Tyr Lys Ala Arg Leu Leu Ala Asp Gly
65                  70                  75                  80 act gcc ggc att gcc gag ctg ggc ttc tcc ggg gta cag ggc gag gac   288
Thr Ala Gly Ile Ala Glu Leu Gly Phe Ser Gly Val Gln Gly Glu Asp
                85                  90                  95 atg gtc att ctg gaa aac acc ccc gcc gtc cac aac gtc gtc gtt tgc   336
Met Val Ile Leu Glu Asn Thr Pro Ala Val His Asn Val Val Val Cys
            100                 105                 110 acc ttg tgc tct tgc tac cca tgg ccg acg ctg ggc ttg ccc cct gcc   384
Thr Leu Cys Ser Cys Tyr Pro Trp Pro Thr Leu Gly Leu Pro Pro Ala
        115                 120                 125 tgg tac aag gcc ccg ccc tac cgg tcc cgc atg gtg agc gac ccg cgt   432
Trp Tyr Lys Ala Pro Pro Tyr Arg Ser Arg Met Val Ser Asp Pro Arg
    130                 135                 140 ggg gtt ctc gcg gag ttc ggc ctg gtg atc ccc gcg aag gaa atc cgc   480
Gly Val Leu Ala Glu Phe Gly Leu Val Ile Pro Ala Lys Glu Ile Arg
145                 150                 155                 160 gtc tgg gac acc acg gcc gaa ttg cgc tac atg gtg ctg ccg gaa cgg   528
Val Trp Asp Thr Thr Ala Glu Leu Arg Tyr Met Val Leu Pro Glu Arg
                165                 170                 175 ccc gcg gga act gaa gcc tac agc gaa gaa caa ctg gcc gaa ctc gtt   576
Pro Ala Gly Thr Glu Ala Tyr Ser Glu Glu Gln Leu Ala Glu Leu Val
            180                 185                 190 acc cgc gat tcg atg atc ggc acc ggc ctg ccc atc caa ccc acc cca   624
Thr Arg Asp Ser Met Ile Gly Thr Gly Leu Pro Ile Gln Pro Thr Pro
        195                 200                 205 tct cat taa                                                        633
Ser His
    210

<210> SEQ ID NO 6
<211> LENGTH: 210
<212> TYPE: PRT
<213> ORGANISM: Comamonas testosteroni 5-MGAM-4D
```

<400> SEQUENCE: 6

```
Met Gly Gln Ser His Thr His Asp His His Asp Gly Tyr Gln Ala
1               5                   10                  15

Pro Pro Glu Asp Ile Ala Leu Arg Val Lys Ala Leu Glu Ser Leu Leu
            20                  25                  30

Ile Glu Lys Gly Leu Val Asp Pro Ala Ala Met Asp Leu Val Val Gln
        35                  40                  45

Thr Tyr Glu His Lys Val Gly Pro Arg Asn Gly Ala Lys Val Val Ala
    50                  55                  60

Lys Ala Trp Val Asp Pro Ala Tyr Lys Ala Arg Leu Leu Ala Asp Gly
65                  70                  75                  80

Thr Ala Gly Ile Ala Glu Leu Gly Phe Ser Gly Val Gln Gly Glu Asp
                85                  90                  95

Met Val Ile Leu Glu Asn Thr Pro Ala Val His Asn Val Val Val Cys
            100                 105                 110

Thr Leu Cys Ser Cys Tyr Pro Trp Pro Thr Leu Gly Leu Pro Pro Ala
        115                 120                 125

Trp Tyr Lys Ala Pro Pro Tyr Arg Ser Arg Met Val Ser Asp Pro Arg
130                 135                 140

Gly Val Leu Ala Glu Phe Gly Leu Val Ile Pro Ala Lys Glu Ile Arg
145                 150                 155                 160

Val Trp Asp Thr Thr Ala Glu Leu Arg Tyr Met Val Leu Pro Glu Arg
                165                 170                 175

Pro Ala Gly Thr Glu Ala Tyr Ser Glu Glu Gln Leu Ala Glu Leu Val
            180                 185                 190

Thr Arg Asp Ser Met Ile Gly Thr Gly Leu Pro Ile Gln Pro Thr Pro
        195                 200                 205

Ser His
    210
```

<210> SEQ ID NO 7
<211> LENGTH: 657
<212> TYPE: DNA
<213> ORGANISM: Comamonas testosteroni 5-MGAM-4D
<220> FEATURE:
<221> NAME/KEY: CDS
<222> LOCATION: (1)..(657)

<400> SEQUENCE: 7

```
atg aat ggc att cac gat act ggg gga gca cat ggt tat ggg ccg gtt      48
Met Asn Gly Ile His Asp Thr Gly Gly Ala His Gly Tyr Gly Pro Val
1               5                   10                  15 tac aga gaa ccg aac gaa ccc gtc ttt cgc tac gac tgg gaa aaa acg      96
Tyr Arg Glu Pro Asn Glu Pro Val Phe Arg Tyr Asp Trp Glu Lys Thr
            20                  25                  30 gtc atg tcc ctg ttc ccg gcg ctg ttc gcc aac ggc aac ttc aac ctc     144
Val Met Ser Leu Phe Pro Ala Leu Phe Ala Asn Gly Asn Phe Asn Leu
        35                  40                  45 gat gag ttt cga cac ggc atc gag cgc atg aac ccc atc gac tac ctg     192
Asp Glu Phe Arg His Gly Ile Glu Arg Met Asn Pro Ile Asp Tyr Leu
    50                  55                  60 aag gga acc tac tac gaa cac tgg atc cat tcc atc gaa acc ttg ctg     240
Lys Gly Thr Tyr Tyr Glu His Trp Ile His Ser Ile Glu Thr Leu Leu
65                  70                  75                  80 gtc gaa aag ggt gtg ctc acg gca acg gaa ctc gcg acc ggc aag gca     288
Val Glu Lys Gly Val Leu Thr Ala Thr Glu Leu Ala Thr Gly Lys Ala
                85                  90                  95 tct ggc aag aca gcg aca ccg gtg ctg acg ccg gcc atc gtg gac gga     336
```

```
                                                              -continued

Ser Gly Lys Thr Ala Thr Pro Val Leu Thr Pro Ala Ile Val Asp Gly
            100                 105                 110 ctg ctc agc acc ggg gct tct gcc gcc cgg gag gag ggt gcg cgg gcg      384
Leu Leu Ser Thr Gly Ala Ser Ala Ala Arg Glu Glu Gly Ala Arg Ala
            115                 120                 125 cgg ttc gct gtg ggg gac aag gtt cgc gtc ctc aac aag aac ccg gtg      432
Arg Phe Ala Val Gly Asp Lys Val Arg Val Leu Asn Lys Asn Pro Val
            130                 135                 140 ggc cat acc cgc atg ccg cgc tac acg cgg ggc aaa gtg ggg aca gtg      480
Gly His Thr Arg Met Pro Arg Tyr Thr Arg Gly Lys Val Gly Thr Val
145                 150                 155                 160 gtc atc gac cat ggt gtg ttc gtg acg ccg gac acc gcg gca cac gga      528
Val Ile Asp His Gly Val Phe Val Thr Pro Asp Thr Ala Ala His Gly
                165                 170                 175 aag ggc gag cac ccc cag cac gtt tac acc gtg agt ttc acg tcg gtc      576
Lys Gly Glu His Pro Gln His Val Tyr Thr Val Ser Phe Thr Ser Val
            180                 185                 190 gaa ctg tgg ggg caa gac gcc tcc tcg ccg aag gac acg att cgc gtc      624
Glu Leu Trp Gly Gln Asp Ala Ser Ser Pro Lys Asp Thr Ile Arg Val
            195                 200                 205 gac ttg tgg gat gac tac ctg gag cca gcg tga                          657
Asp Leu Trp Asp Asp Tyr Leu Glu Pro Ala
            210                 215

<210> SEQ ID NO 8
<211> LENGTH: 218
<212> TYPE: PRT
<213> ORGANISM: Comamonas testosteroni 5-MGAM-4D

<400> SEQUENCE: 8

Met Asn Gly Ile His Asp Thr Gly Gly Ala His Gly Tyr Gly Pro Val
1               5                   10                  15

Tyr Arg Glu Pro Asn Glu Pro Val Phe Arg Tyr Asp Trp Glu Lys Thr
            20                  25                  30

Val Met Ser Leu Phe Pro Ala Leu Phe Ala Asn Gly Asn Phe Asn Leu
        35                  40                  45

Asp Glu Phe Arg His Gly Ile Glu Arg Met Asn Pro Ile Asp Tyr Leu
    50                  55                  60

Lys Gly Thr Tyr Tyr Glu His Trp Ile His Ser Ile Glu Thr Leu Leu
65                  70                  75                  80

Val Glu Lys Gly Val Leu Thr Ala Thr Glu Leu Ala Thr Gly Lys Ala
                85                  90                  95

Ser Gly Lys Thr Ala Thr Pro Val Leu Thr Pro Ala Ile Val Asp Gly
            100                 105                 110

Leu Leu Ser Thr Gly Ala Ser Ala Ala Arg Glu Glu Gly Ala Arg Ala
            115                 120                 125

Arg Phe Ala Val Gly Asp Lys Val Arg Val Leu Asn Lys Asn Pro Val
            130                 135                 140

Gly His Thr Arg Met Pro Arg Tyr Thr Arg Gly Lys Val Gly Thr Val
145                 150                 155                 160

Val Ile Asp His Gly Val Phe Val Thr Pro Asp Thr Ala Ala His Gly
                165                 170                 175

Lys Gly Glu His Pro Gln His Val Tyr Thr Val Ser Phe Thr Ser Val
            180                 185                 190

Glu Leu Trp Gly Gln Asp Ala Ser Ser Pro Lys Asp Thr Ile Arg Val
            195                 200                 205

Asp Leu Trp Asp Asp Tyr Leu Glu Pro Ala
            210                 215
```

<210> SEQ ID NO 9
<211> LENGTH: 1407
<212> TYPE: DNA
<213> ORGANISM: Comamonas testosteroni 5-MGAM-4D
<220> FEATURE:
<221> NAME/KEY: CDS
<222> LOCATION: (1)..(1407)

<400> SEQUENCE: 9

| | | | | | | | | | | | | | | | | |
|---|---|---|---|---|---|---|---|---|---|---|---|---|---|---|---|---|
| atg | agt | tcg | cta | acc | cgc | ctc | acc | ctc | gcg | caa | gtt | gcg | cag | aaa | ctt | 48 |
| Met | Ser | Ser | Leu | Thr | Arg | Leu | Thr | Leu | Ala | Gln | Val | Ala | Gln | Lys | Leu | |
| 1 | | | 5 | | | | | 10 | | | | | 15 | | | |
| aag | gca | cgg | gaa | gtc | tcc | gcc | gtt | gaa | gtt | ctg | gac | gcc | tgt | ctg | acg | 96 |
| Lys | Ala | Arg | Glu | Val | Ser | Ala | Val | Glu | Val | Leu | Asp | Ala | Cys | Leu | Thr | |
| | | | 20 | | | | | 25 | | | | | 30 | | | |
| cag | gtg | cgc | tcc | acc | gaa | aaa | cag | atc | agt | gcg | tac | gtg | tgc | gtg | ctg | 144 |
| Gln | Val | Arg | Ser | Thr | Glu | Lys | Gln | Ile | Ser | Ala | Tyr | Val | Cys | Val | Leu | |
| | | 35 | | | | | 40 | | | | | 45 | | | | |
| gag | gat | cag | gcc | cgt | gca | gca | gcc | cag | caa | gct | gac | gcc | gac | atc | agc | 192 |
| Glu | Asp | Gln | Ala | Arg | Ala | Ala | Ala | Gln | Gln | Ala | Asp | Ala | Asp | Ile | Ser | |
| 50 | | | | 55 | | | | | 60 | | | | | | | |
| gcc | ggg | cgc | tgg | aaa | ggc | ccg | ctg | cat | ggc | gtg | cct | gta | gcg | gtc | aag | 240 |
| Ala | Gly | Arg | Trp | Lys | Gly | Pro | Leu | His | Gly | Val | Pro | Val | Ala | Val | Lys | |
| 65 | | | | 70 | | | | | 75 | | | | | 80 | | |
| gac | tta | tac | gac | atc | gct | ggc | gta | ccc | acc | acg | gca | tcg | tcg | cgc | cag | 288 |
| Asp | Leu | Tyr | Asp | Ile | Ala | Gly | Val | Pro | Thr | Thr | Ala | Ser | Ser | Arg | Gln | |
| | | | | 85 | | | | | 90 | | | | | 95 | | |
| cgc | acg | aat | tgg | acg | ccg | cag | caa | gac | tgc | gcc | gta | gtc | cgg | cgc | ttg | 336 |
| Arg | Thr | Asn | Trp | Thr | Pro | Gln | Gln | Asp | Cys | Ala | Val | Val | Arg | Arg | Leu | |
| | | | 100 | | | | | 105 | | | | | 110 | | | |
| aaa | gac | gca | ggt | gcc | gtt | atc | ctt | ggc | aag | acc | cat | acg | cac | gaa | ttc | 384 |
| Lys | Asp | Ala | Gly | Ala | Val | Ile | Leu | Gly | Lys | Thr | His | Thr | His | Glu | Phe | |
| | | 115 | | | | | 120 | | | | | 125 | | | | |
| gcc | tat | ggc | gtc | atc | act | ccg | aag | tcg | cgc | aac | ccc | tgg | gac | ccg | gga | 432 |
| Ala | Tyr | Gly | Val | Ile | Thr | Pro | Lys | Ser | Arg | Asn | Pro | Trp | Asp | Pro | Gly | |
| | 130 | | | | | 135 | | | | | 140 | | | | | |
| aga | aca | ccg | ggt | ggc | tcc | agc | ggc | ggc | tcg | gcg | gcc | acg | gtc | gca | gcc | 480 |
| Arg | Thr | Pro | Gly | Gly | Ser | Ser | Gly | Gly | Ser | Ala | Ala | Thr | Val | Ala | Ala | |
| 145 | | | | | 150 | | | | | 155 | | | | | 160 | |
| tgc | ggc | gtc | tac | ttg | gcg | acc | ggc | acc | gac | acc | ggt | gga | tcc | gtt | cgc | 528 |
| Cys | Gly | Val | Tyr | Leu | Ala | Thr | Gly | Thr | Asp | Thr | Gly | Gly | Ser | Val | Arg | |
| | | | | 165 | | | | | 170 | | | | | 175 | | |
| atc | cct | tcg | tcg | atg | tgc | aac | acc | gta | ggc | ctg | aag | cca | acc | tac | ggg | 576 |
| Ile | Pro | Ser | Ser | Met | Cys | Asn | Thr | Val | Gly | Leu | Lys | Pro | Thr | Tyr | Gly | |
| | | | 180 | | | | | 185 | | | | | 190 | | | |
| cgc | gtg | agc | cgt | gcc | ggt | gtg | agt | tca | ctt | tcc | tgg | agc | ctg | gac | cat | 624 |
| Arg | Val | Ser | Arg | Ala | Gly | Val | Ser | Ser | Leu | Ser | Trp | Ser | Leu | Asp | His | |
| | | 195 | | | | | 200 | | | | | 205 | | | | |
| cca | ggc | ccg | atc | acg | cgc | acc | gtg | gaa | gac | acg | gcg | ctc | agc | ctt | cag | 672 |
| Pro | Gly | Pro | Ile | Thr | Arg | Thr | Val | Glu | Asp | Thr | Ala | Leu | Ser | Leu | Gln | |
| | 210 | | | | | 215 | | | | | 220 | | | | | |
| gtg | atg | gct | ggc | ttc | gat | cca | gcc | gac | cgc | ggc | tcg | ttg | gat | gag | ccg | 720 |
| Val | Met | Ala | Gly | Phe | Asp | Pro | Ala | Asp | Arg | Gly | Ser | Leu | Asp | Glu | Pro | |
| 225 | | | | | 230 | | | | | 235 | | | | | 240 | |
| gtg | ccc | agc | tat | gcc | gaa | ggg | ctc | ggc | caa | ggc | gtg | aaa | ggc | ctg | cgc | 768 |
| Val | Pro | Ser | Tyr | Ala | Glu | Gly | Leu | Gly | Gln | Gly | Val | Lys | Gly | Leu | Arg | |
| | | | | 245 | | | | | 250 | | | | | 255 | | |
| gtg | ggc | gtg | ccg | aag | aac | tac | ttc | ttc | gac | cgc | gtg | gac | ccg | gaa | gtt | 816 |
| Val | Gly | Val | Pro | Lys | Asn | Tyr | Phe | Phe | Asp | Arg | Val | Asp | Pro | Glu | Val | |
| | | | | 260 | | | | | 265 | | | | | 270 | | |

-continued

| | |
|---|---|
| gaa agt gcg gtt cgt gcc gcc atc gat caa ctg aaa gag ctg ggc gcc<br>Glu Ser Ala Val Arg Ala Ala Ile Asp Gln Leu Lys Glu Leu Gly Ala<br>275                 280                 285 | 864 |
| gaa ctg gtg gaa gtc gaa gtg ccc atg gcc gag cag atc atc ccg gtg<br>Glu Leu Val Glu Val Glu Val Pro Met Ala Glu Gln Ile Ile Pro Val<br>290                 295                 300 | 912 |
| gag ttc ggg atc gtg cta ccc gaa gcc agc gcc tac cac cgc acg atg<br>Glu Phe Gly Ile Val Leu Pro Glu Ala Ser Ala Tyr His Arg Thr Met<br>305                 310                 315                 320 | 960 |
| ctg cgc gag tca ccc gag ctc tac acc gcc gat gtc cgc ata ctg ctg<br>Leu Arg Glu Ser Pro Glu Leu Tyr Thr Ala Asp Val Arg Ile Leu Leu<br>                325                 330                 335 | 1008 |
| gaa ctc gga aat cta gtc acc gcc acc gac tac ctg cag gcg cag cgc<br>Glu Leu Gly Asn Leu Val Thr Ala Thr Asp Tyr Leu Gln Ala Gln Arg<br>                340                 345                 350 | 1056 |
| gtc cgt acg ctg atg cag cgc gcg gtg gcc gag atg ttc cag cgc atc<br>Val Arg Thr Leu Met Gln Arg Ala Val Ala Glu Met Phe Gln Arg Ile<br>                355                 360                 365 | 1104 |
| gat gtg ctg atc gca ccc aca ctg ccc atc ccg gct gct cgc agc ggg<br>Asp Val Leu Ile Ala Pro Thr Leu Pro Ile Pro Ala Ala Arg Ser Gly<br>370                 375                 380 | 1152 |
| gag gag gtc cac aca tgg ccg gac ggc acg gta gag gcg ttg ttc atg<br>Glu Glu Val His Thr Trp Pro Asp Gly Thr Val Glu Ala Leu Phe Met<br>385                 390                 395                 400 | 1200 |
| gcc tat acg cgc ttc acc tcg ttc ggc aac gtg aca gga tta ccc acg<br>Ala Tyr Thr Arg Phe Thr Ser Phe Gly Asn Val Thr Gly Leu Pro Thr<br>                405                 410                 415 | 1248 |
| ctg aac ctg ccc tgt ggt ttc tcc aag gat ggg ttg ccg atc ggc atg<br>Leu Asn Leu Pro Cys Gly Phe Ser Lys Asp Gly Leu Pro Ile Gly Met<br>                420                 425                 430 | 1296 |
| cag atc acc ggc cgg ccg ctg gac gag aag acc ctg ctg cgt gct ggg<br>Gln Ile Thr Gly Arg Pro Leu Asp Glu Lys Thr Leu Leu Arg Ala Gly<br>                435                 440                 445 | 1344 |
| ctg gcc tac gag aaa gcc acg acc tgg cac cag cgt cat ccg gaa ctg<br>Leu Ala Tyr Glu Lys Ala Thr Thr Trp His Gln Arg His Pro Glu Leu<br>450                 455                 460 | 1392 |
| atc gga gcg ggc tga<br>Ile Gly Ala Gly<br>465 | 1407 |

<210> SEQ ID NO 10
<211> LENGTH: 468
<212> TYPE: PRT
<213> ORGANISM: Comamonas testosteroni 5-MGAM-4D

<400> SEQUENCE: 10

Met Ser Ser Leu Thr Arg Leu Thr Leu Ala Gln Val Ala Gln Lys Leu
1               5                   10                  15

Lys Ala Arg Glu Val Ser Ala Val Glu Val Leu Asp Ala Cys Leu Thr
            20                  25                  30

Gln Val Arg Ser Thr Glu Lys Gln Ile Ser Ala Tyr Val Cys Val Leu
        35                  40                  45

Glu Asp Gln Ala Arg Ala Ala Gln Gln Ala Asp Ala Asp Ile Ser
    50                  55                  60

Ala Gly Arg Trp Lys Gly Pro Leu His Gly Val Pro Ala Val Lys
65                  70                  75                  80

Asp Leu Tyr Asp Ile Ala Gly Val Pro Thr Thr Ala Ser Ser Arg Gln
                85                  90                  95

Arg Thr Asn Trp Thr Pro Gln Gln Asp Cys Ala Val Val Arg Arg Leu
            100                 105                 110

```
Lys Asp Ala Gly Ala Val Ile Leu Gly Lys Thr His Thr His Glu Phe
            115                 120                 125
Ala Tyr Gly Val Ile Thr Pro Lys Ser Arg Asn Pro Trp Asp Pro Gly
        130                 135                 140
Arg Thr Pro Gly Gly Ser Ser Gly Gly Ser Ala Ala Thr Val Ala Ala
145                 150                 155                 160
Cys Gly Val Tyr Leu Ala Thr Gly Thr Asp Thr Gly Gly Ser Val Arg
                165                 170                 175
Ile Pro Ser Ser Met Cys Asn Thr Val Gly Leu Lys Pro Thr Tyr Gly
            180                 185                 190
Arg Val Ser Arg Ala Gly Val Ser Ser Leu Ser Trp Ser Leu Asp His
        195                 200                 205
Pro Gly Pro Ile Thr Arg Thr Val Glu Asp Thr Ala Leu Ser Leu Gln
    210                 215                 220
Val Met Ala Gly Phe Asp Pro Ala Asp Arg Gly Ser Leu Asp Glu Pro
225                 230                 235                 240
Val Pro Ser Tyr Ala Glu Gly Leu Gly Gln Gly Val Lys Gly Leu Arg
                245                 250                 255
Val Gly Val Pro Lys Asn Tyr Phe Phe Asp Arg Val Asp Pro Glu Val
            260                 265                 270
Glu Ser Ala Val Arg Ala Ala Ile Asp Gln Leu Lys Glu Leu Gly Ala
        275                 280                 285
Glu Leu Val Glu Val Glu Val Pro Met Ala Glu Gln Ile Ile Pro Val
    290                 295                 300
Glu Phe Gly Ile Val Leu Pro Glu Ala Ser Ala Tyr His Arg Thr Met
305                 310                 315                 320
Leu Arg Glu Ser Pro Glu Leu Tyr Thr Ala Asp Val Arg Ile Leu Leu
                325                 330                 335
Glu Leu Gly Asn Leu Val Thr Ala Thr Asp Tyr Leu Gln Ala Gln Arg
            340                 345                 350
Val Arg Thr Leu Met Gln Arg Ala Val Ala Glu Met Phe Gln Arg Ile
        355                 360                 365
Asp Val Leu Ile Ala Pro Thr Leu Pro Ile Pro Ala Ala Arg Ser Gly
    370                 375                 380
Glu Glu Val His Thr Trp Pro Asp Gly Thr Val Glu Ala Leu Phe Met
385                 390                 395                 400
Ala Tyr Thr Arg Phe Thr Ser Phe Gly Asn Val Thr Gly Leu Pro Thr
                405                 410                 415
Leu Asn Leu Pro Cys Gly Phe Ser Lys Asp Gly Leu Pro Ile Gly Met
            420                 425                 430
Gln Ile Thr Gly Arg Pro Leu Asp Glu Lys Thr Leu Leu Arg Ala Gly
        435                 440                 445
Leu Ala Tyr Glu Lys Ala Thr Thr Trp His Gln Arg His Pro Glu Leu
    450                 455                 460
Ile Gly Ala Gly
465
```